(12) United States Patent
Swisher et al.

(10) Patent No.: US 8,777,930 B2
(45) Date of Patent: Jul. 15, 2014

(54) DISCRIMINATING ORAL-TIP ADAPTOR

(75) Inventors: David Rork Swisher, St. Charles, MO (US); Kimberly A. Moos, Florissant, MO (US); Kevin C. Meier, Affton, MO (US)

(73) Assignee: Covidien LP, Mansfield, MA (US)

( * ) Notice: Subject to any disclaimer, the term of this patent is extended or adjusted under 35 U.S.C. 154(b) by 1360 days.

(21) Appl. No.: 12/495,091

(22) Filed: Jun. 30, 2009

(65) Prior Publication Data

US 2009/0326481 A1 Dec. 31, 2009

Related U.S. Application Data

(60) Provisional application No. 61/077,020, filed on Jun. 30, 2008.

(51) Int. Cl.
*A61M 25/16* (2006.01)
*A61M 39/10* (2006.01)
*A61M 25/00* (2006.01)
*A61M 39/02* (2006.01)
*A61J 15/00* (2006.01)

(52) U.S. Cl.
CPC ....... *A61M 39/10* (2013.01); *A61M 2202/0482* (2013.01); *A61M 2039/1094* (2013.01); *A61M 39/02* (2013.01); *A61J 15/00* (2013.01); *A61J 15/0026* (2013.01); *A61J 15/0092* (2013.01)
USPC ............................. 604/533; 604/284; 604/910

(58) Field of Classification Search
USPC .................. 604/537, 538, 910, 284
See application file for complete search history.

(56) References Cited

U.S. PATENT DOCUMENTS

| 1,954,454 A | 4/1934 | McFarland |
| 3,752,510 A | 8/1973 | Windischman et al. |
| 4,211,439 A | 7/1980 | Moldestad |
| 4,607,868 A | 8/1986 | Harvey et al. |

(Continued)

FOREIGN PATENT DOCUMENTS

| CA | 2741525 A1 | 3/2008 |
| EP | 2269685 A2 | 1/2011 |

(Continued)

OTHER PUBLICATIONS

European Search Report regarding related application serial No. EP 09163772.8 dated Nov. 9, 2009, 7 pgs.

(Continued)

*Primary Examiner* — Nicholas Lucchesi
*Assistant Examiner* — Weng Lee

(57) ABSTRACT

An adaptor for discriminating connection of an oral tip of a source of liquid enteral product to a feeding line. In one embodiment, the adaptor includes an internal stop in the body having a contact surface that is angled with respect to a transverse plane extending generally transverse to the longitudinal axis of the connection port so that if the standard luer tip is inserted into the connection port, the luer tip does not make flush contact with the contact surface. In another embodiment, the adaptor includes an external stop surrounding the connection port generally adjacent to the first open end of the body. The adaptor may include an umbrella valve. In other embodiments, the adaptor includes a fluid release opening in fluid communication with the connection port extending generally radially through the adaptor body at a location spaced from the longitudinal ends of the body.

11 Claims, 39 Drawing Sheets

(56) References Cited

U.S. PATENT DOCUMENTS

| | | |
|---|---|---|
| 4,617,012 A | 10/1986 | Vaillancourt |
| 4,619,640 A | 10/1986 | Potolsky et al. |
| 5,017,188 A | 5/1991 | Marten et al. |
| 5,032,116 A | 7/1991 | Peterson et al. |
| 5,057,093 A | 10/1991 | Clegg et al. |
| 5,242,425 A | 9/1993 | White et al. |
| 5,267,983 A | 12/1993 | Oilschlager et al. |
| 5,355,876 A | 10/1994 | Brodsky et al. |
| 5,395,348 A | 3/1995 | Ryan |
| 5,725,511 A | 3/1998 | Urrutia |
| 5,925,028 A | 7/1999 | Delvigo |
| 6,402,207 B1 | 6/2002 | Segal et al. |
| 6,464,686 B1 | 10/2002 | O'Hara et al. |
| 6,467,651 B1 | 10/2002 | Muderlak et al. |
| 6,612,624 B1 | 9/2003 | Segal et al. |
| 6,673,059 B2 | 1/2004 | Guala |
| 6,745,998 B2 | 6/2004 | Doyle |
| 6,874,522 B2 | 4/2005 | Anderson et al. |
| 6,979,322 B2 * | 12/2005 | Chu et al. .................... 604/248 |
| 7,140,592 B2 | 11/2006 | Phillips |
| 7,240,926 B2 | 7/2007 | Dalle et al. |
| 7,523,967 B2 * | 4/2009 | Steppe ........................ 285/401 |
| 7,611,317 B2 | 11/2009 | Muderlak et al. |
| 7,914,519 B2 * | 3/2011 | Moran et al. ................. 604/534 |
| 8,066,688 B2 | 11/2011 | Zinger et al. |
| 8,257,286 B2 * | 9/2012 | Meyer et al. .................. 601/148 |
| 2002/0128607 A1 | 9/2002 | Haury et al. |
| 2004/0034324 A1 | 2/2004 | Seese et al. |
| 2005/0090805 A1 | 4/2005 | Shaw et al. |
| 2006/0108555 A1 | 5/2006 | Kiehne |
| 2006/0142735 A1 | 6/2006 | Whitley |
| 2007/0060898 A1 * | 3/2007 | Shaughnessy et al. ....... 604/284 |
| 2008/0103486 A1 | 5/2008 | Owens |
| 2008/0140020 A1 | 6/2008 | Shirley |
| 2008/0140055 A1 | 6/2008 | Shirley |
| 2008/0318456 A1 | 12/2008 | Yow et al. |
| 2009/0099552 A1 | 4/2009 | Levy et al. |

FOREIGN PATENT DOCUMENTS

| | | |
|---|---|---|
| JP | 63111146 U | 7/1988 |
| JP | 2001299906 A | 10/2001 |
| JP | 2001299936 A | 10/2001 |
| JP | 2002028224 A | 1/2002 |
| JP | 2002078797 A | 3/2002 |
| WO | 2007030403 A2 | 3/2007 |
| WO | 2008049568 A1 | 5/2008 |

OTHER PUBLICATIONS

Office Action dated Aug. 9, 2013, Japanese Patent Application No. 2009-153175, 4 pages.

* cited by examiner

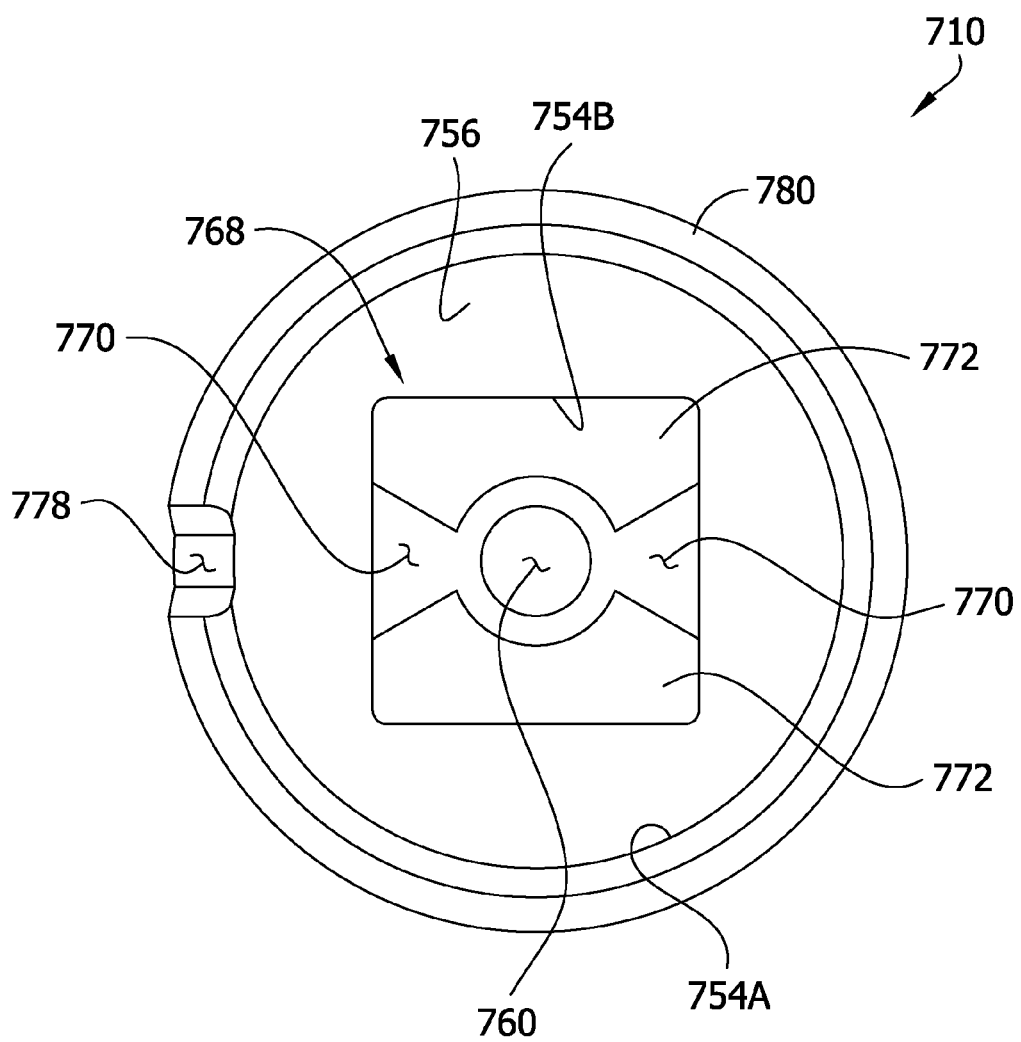

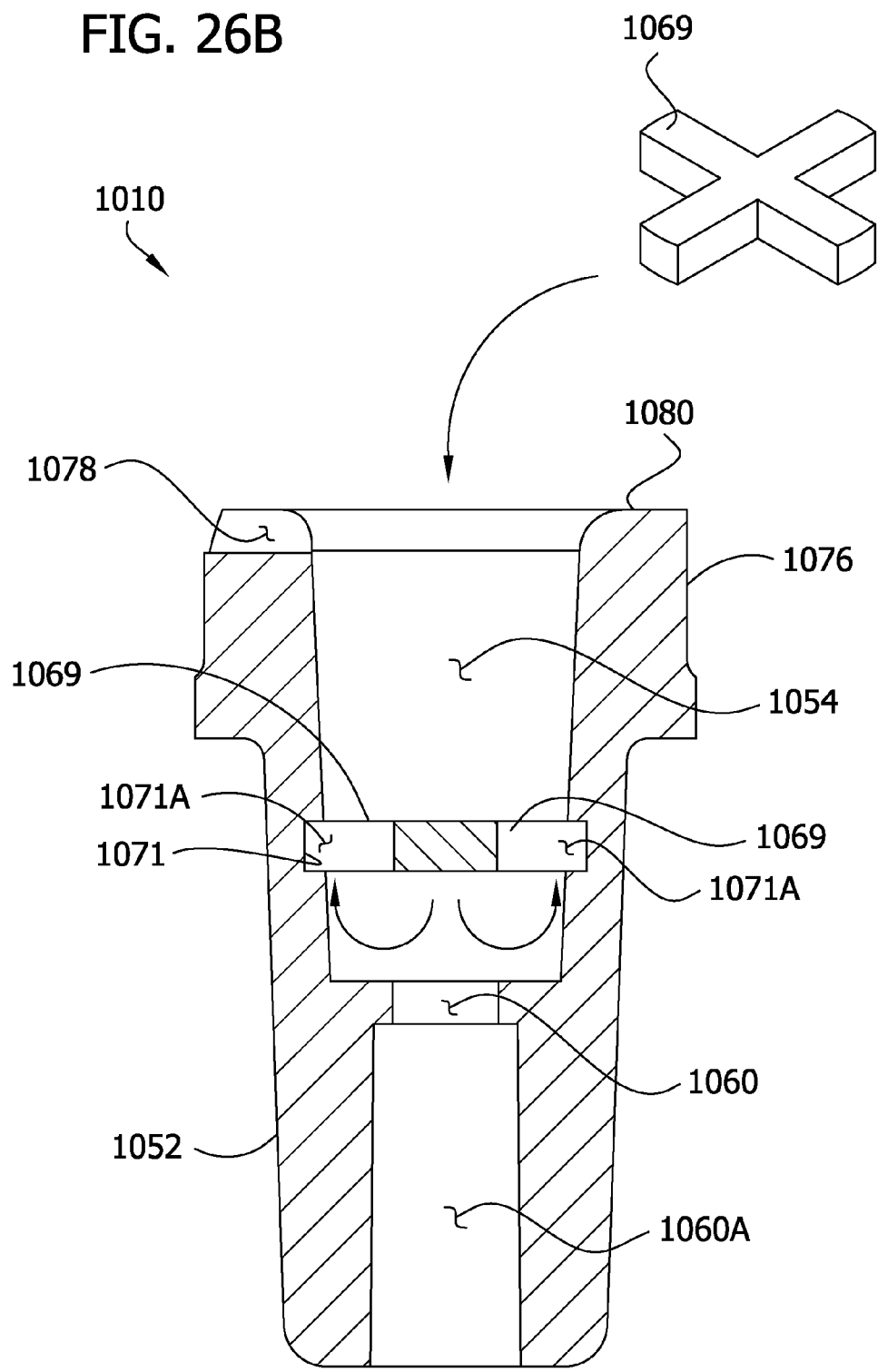

DISCRIMINATING ORAL-TIP ADAPTOR

CROSS-REFERENCE TO RELATED APPLICATIONS

The present application claims priority to U.S. Provisional Application No. 61/077,020, filed Jun. 30, 2008, the entirety of which is herein incorporated by reference.

FIELD OF THE INVENTION

The present invention generally relates to a discriminating oral-tip adaptor.

BACKGROUND OF THE INVENTION

Tubing and catheter misconnections are a serious problem in hospitals. One type of tube and catheter misconnection error involves enteral feeding tubes and intravenous catheters. Enteral feeding tubes are used to administer liquid nutritional solutions and medications directly to a patient's gastrointestinal system. In contrast, intravenous catheters are used to administer liquid nutritional solutions and medications directly to a patient's vascular system. Patients may be harmed if feeding solutions are administered intravenously and vice versa. Errors such as this occur because of medical professionals using similar or identical tubing for different purposes. For example, luer tips, including luer-lock components, contribute to many of these errors because they enable functionally dissimilar tubes or catheters to be connected. In other words, a luer tip may be inserted improperly into a connector or adaptor of a feeding tube, with potential harmful results.

Connectors for different medical equipment may be given different sizes to avoid unintended connection. For example, an enteral feeding system may be sized for oral tip connection. Male oral tip connectors will not make ready connection with female luer connectors, such as commonly found for intravenous use. Typically, male luer tip connectors would not be able to make sealing connection with a female oral connector.

SUMMARY OF THE INVENTION

In one aspect, an adaptor for discriminating connection of an oral tip of a source of liquid enteral product to a feeding line and preventing sealed connection with a standard luer tip generally comprises a body having first and second open ends. A connection port has a longitudinal axis extending into the body from the first open end. The connection port is defined by an interior wall of the body and is sized and shaped to sealingly receive an oral tip and to prevent sealing connection with the standard luer tip. A fluid outlet passage extends from the connection port inside the body to the second open end of the body. An internal stop in the body has a contact surface that is angled with respect to a transverse plane extending generally transverse to the longitudinal axis of the connection port so that if the standard luer tip is inserted into the connection port, the luer tip does not make flush contact with the contact surface.

In another aspect, an adaptor for discriminating connection of an oral tip of a source of liquid enteral product to a feeding line and preventing sealed connection with a standard luer tip including a luer-lock sleeve generally comprises a body having first and second open longitudinal ends. A connection port extending into the body from the first open end. The connection port is sized and shaped to sealingly receive an oral tip and to prevent sealing connection with the standard luer tip. A fluid outlet passage extends from the connection port inside the body to the second open end of the body. An external stop surrounds the connection port generally adjacent to the first open end of the body. The external stop has a contact surface that is sized and shaped to prevent reception of the stop into a luer-lock sleeve of the standard luer tip so that the luer-lock sleeve generally abuts the external stop if the standard male luer tip is inserted into the connection port through the first open end. The external stop has a fluid release channel in fluid communication with the connection port extending generally radially through the external stop. The contact surface has a larger surface area than the projected area of the release channel in the plane of the contact surface.

In yet another aspect, an adaptor for discriminating connection of an oral tip of a source of liquid enteral product to a feeding line and preventing sealed connection with a standard luer tip generally comprises a body having first and second open ends. A connection port extends into the body from the first open end to an end of the connection port within the adaptor body, the connection port being defined by an interior wall of the body and being sized and shaped to sealingly receive an oral tip and to prevent sealing connection with the standard luer tip. A fluid outlet passage extends from the connection port inside the body to the second open end of the body. The connection port has a length greater than a length of the standard luer tip, whereby the luer tip does not extend to the end of the connection within the adaptor body.

In another aspect, an adaptor for discriminating connection of an oral tip of a source of liquid enteral product to a feeding line and preventing sealed connection with a standard luer tip including a luer-lock sleeve generally comprises a body having first and second open longitudinal ends. A connection port extends into the body from the first open end. The connection port is sized and shaped to sealingly receive an oral tip and to prevent sealing connection with the standard luer tip. A fluid outlet passage extends from the connection port inside the body to the second open end of the body. A fluid release opening in fluid communication with the connection port extends generally radially through the adaptor body at a location spaced from the longitudinal ends of the body.

In yet another aspect, an adaptor for discriminating connection of an oral tip of a source of liquid enteral product to a feeding line and preventing sealed connection with a standard luer tip generally comprises a body having first and second open ends. A connection port extends into the body from the first open end. The connection port is defined by an interior wall of the body and is sized and shaped to sealingly receive an oral tip and to prevent sealing connection with the standard luer tip. A fluid outlet passage extends from the connection port inside the body to the second open end of the body. An umbrella valve at the second open end of the body prevents liquid flow through the second open end if the standard luer tip is inserted into the connection port and liquid is delivered via the standard luer tip.

Other features will be in part apparent and in part pointed out hereinafter.

BRIEF DESCRIPTION OF THE DRAWINGS

FIG. 24A is a top plan of the adaptor of FIG. 24;

FIG. 26B is a section of a second example of the eleventh embodiment of the discriminating oral-tip adaptor;

Corresponding reference characters indicate corresponding parts throughout the drawings.

DETAILED DESCRIPTION OF THE DRAWINGS

Referring now the drawings, the present invention is directed toward a discriminating fluid adaptor, generally indicated at 10, that is configured for sealed fluid connection with an oral tip associated with a delivery device. In a first embodiment illustrated in FIGS. 1-13, the adaptor 10 is a component of a connector assembly, generally indicated at 12, that is secured to a feeding tube 14. In the embodiments illustrated in FIGS. 14-17, the adaptor 10 is adapted for direct securement to a feeding tube, such as a pediatric feeding tube. The remaining embodiments are of the same basic structure as either the first or the second embodiments. Other configurations of the adaptor 10 are within the scope of the present invention. It is also understood that the features illustrated in each embodiment may be combined with features of one or more of the other embodiments.

Figure 1:
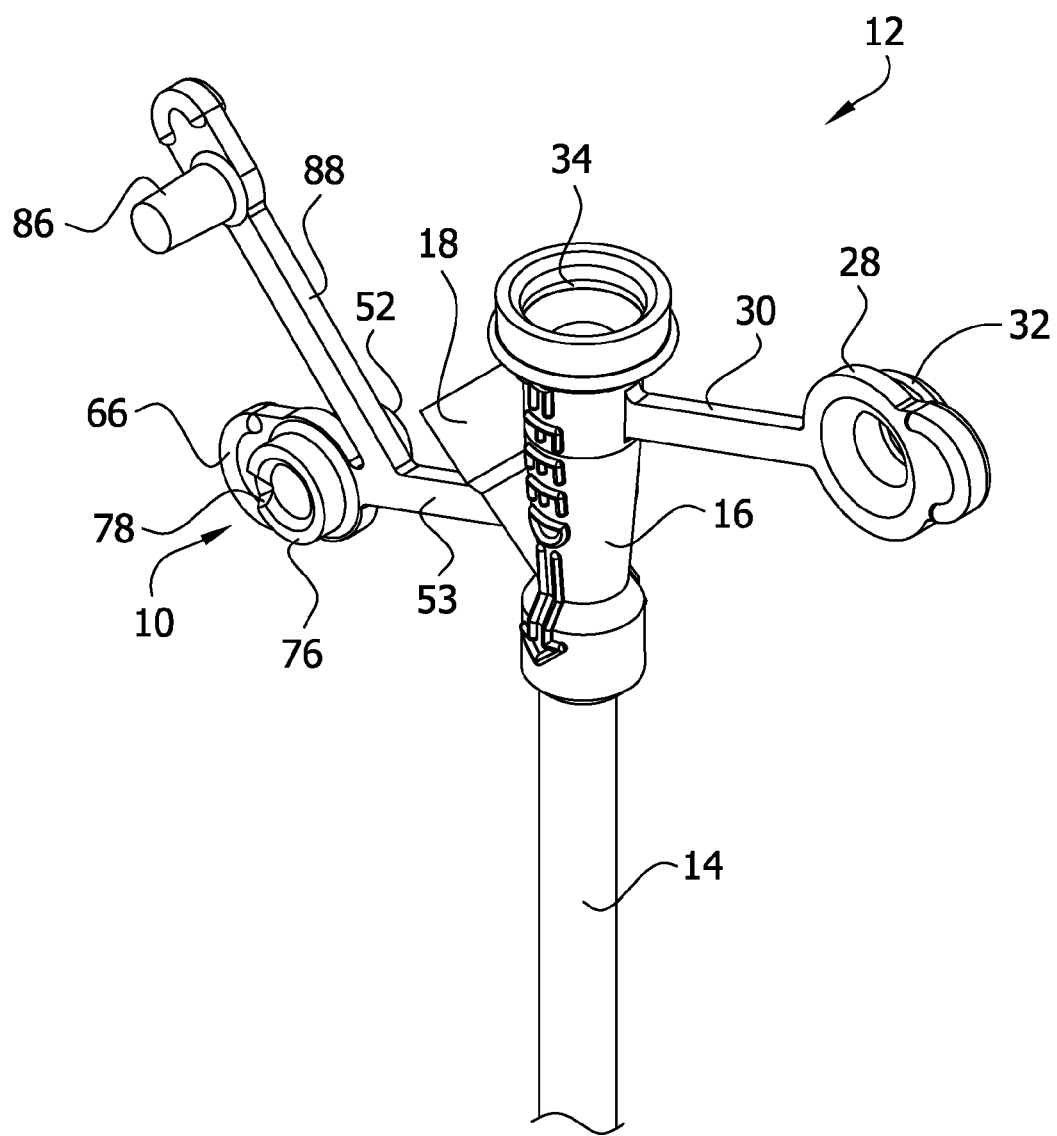
FIG. 1 is a perspective of a connector assembly of an enteral feeding tube, including a first embodiment of a discriminating oral-tip adaptor.
Figure 2:
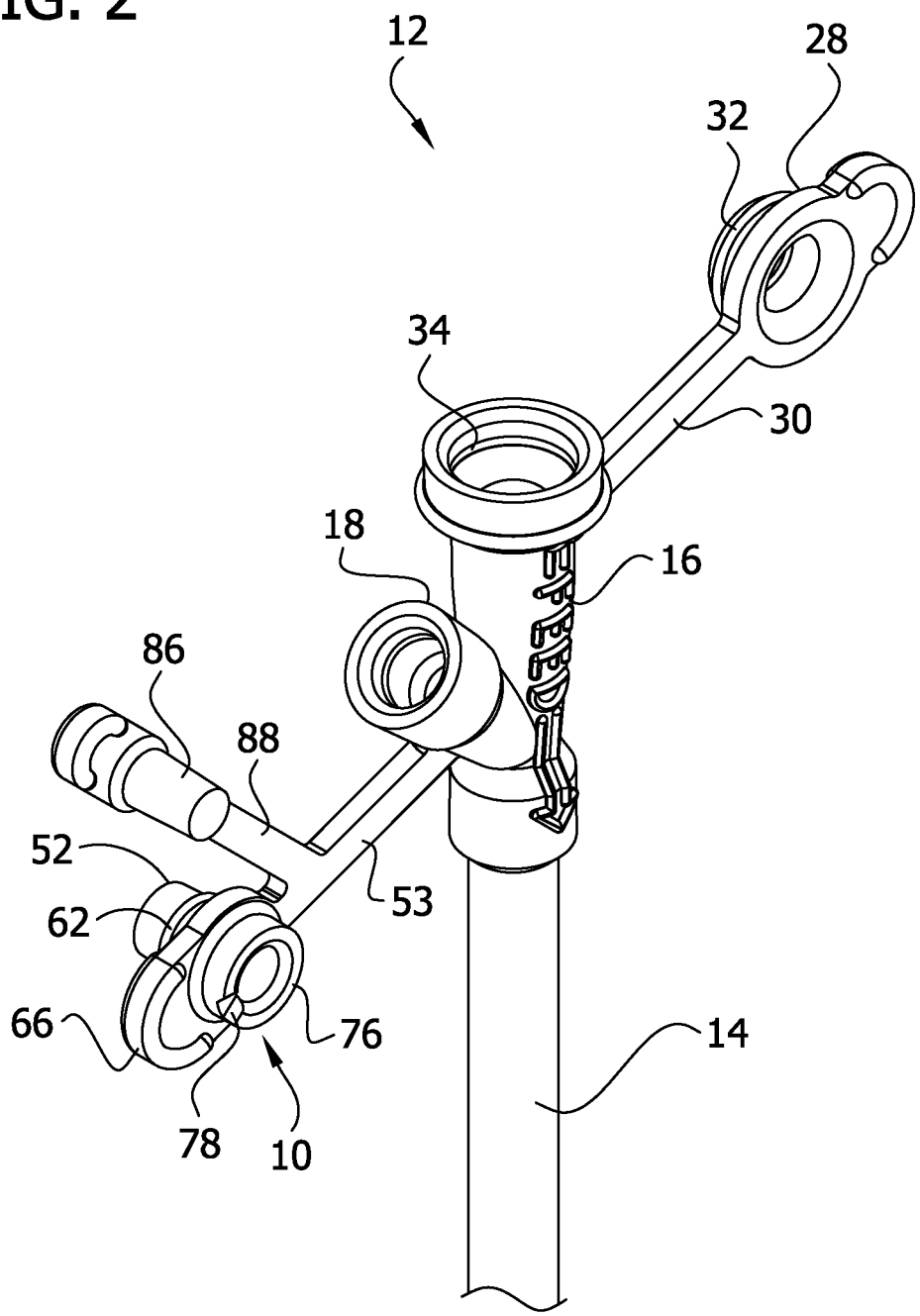
FIG. 2 is a perspective of the connector assembly rotated from the orientation of FIG. 1.
Figure 3:
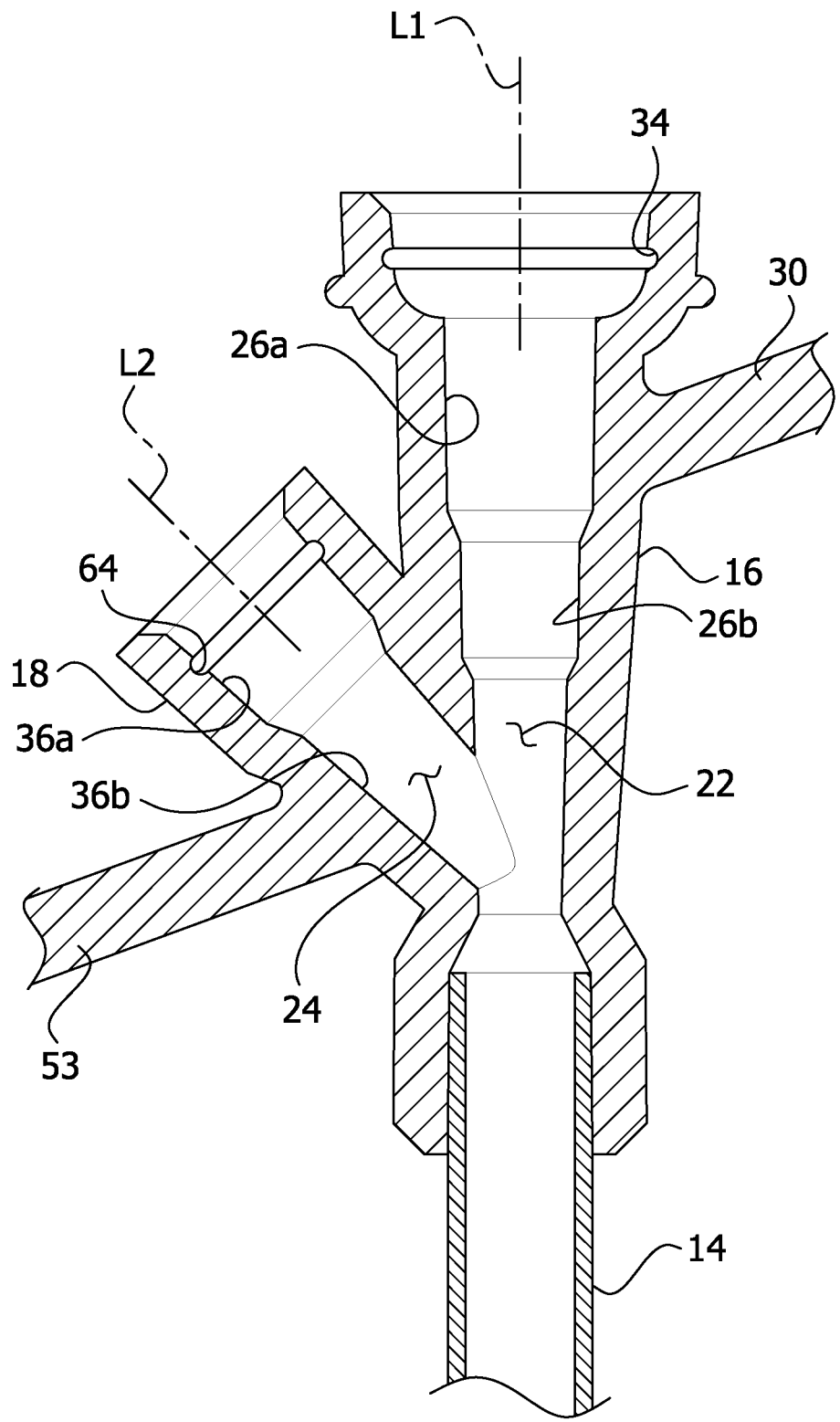
FIG. 3 is an enlarged, fragmentary longitudinal section of the connector assembly.
Figure 4:
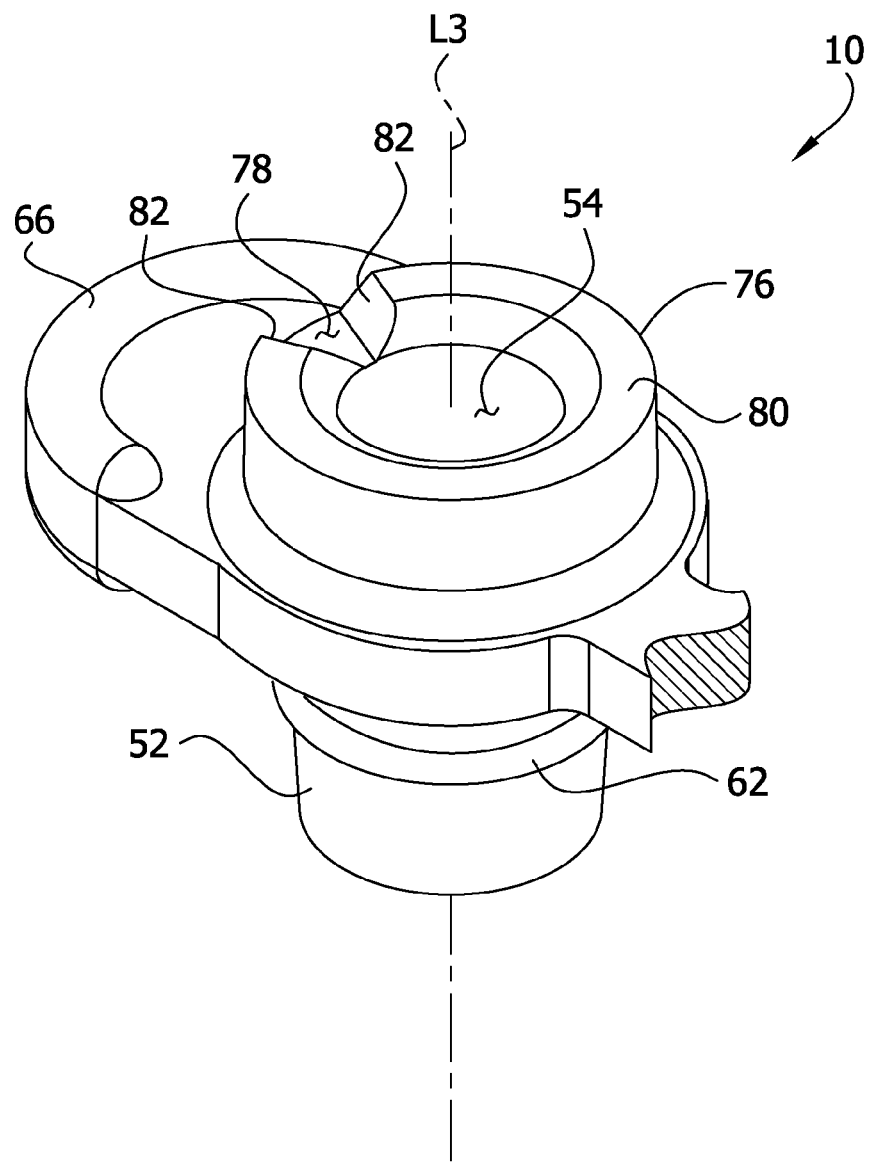
FIG. 4 is an enlarged, perspective of the first embodiment of the discriminating oral-tip adaptor broken away from the connector assembly.
Figure 5:
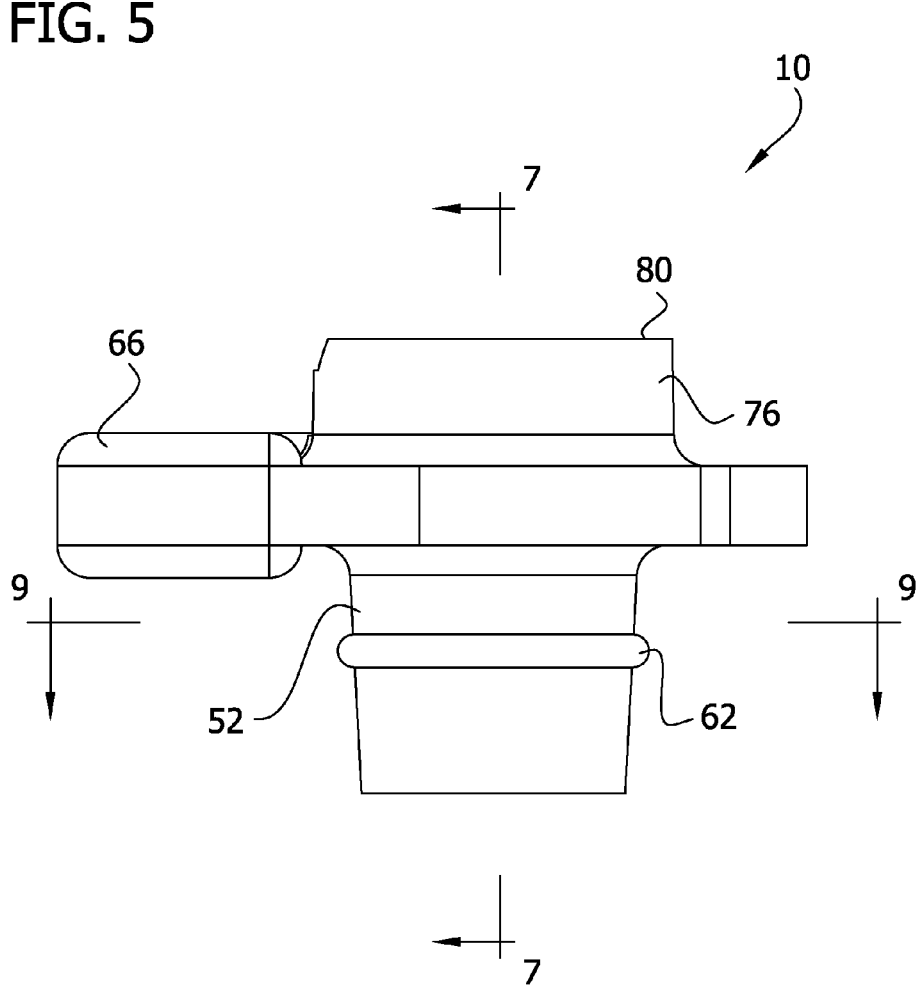
FIG. 5 is a side elevation of the discriminating oral-tip adaptor in FIG. 4.

Referring to the first embodiment, and particularly to FIGS. 1-3, the connector assembly 12 generally comprises, in addition to the adaptor 10, a primary section 16 and a Y-port 18 formed integrally with and extending laterally outward from the primary section. The primary section 16 and the Y-port 18 form a feeding line connector in the illustrated embodiments. Referring to FIG. 3, the primary section 16 includes a primary fluid passage 22 extending along a longitudinal axis L1 of the body, and the Y-port 18 includes an auxiliary fluid passage 24 extending along a longitudinal axis L2 of the Y-port in fluid communication with the main fluid passage. An upstream longitudinal end margin of the primary fluid passage 22 is sized and shaped to receive a male component associated with a primary source of liquid enteral product (not shown) to fluidly connect the source to the primary section. For example, the primary source may comprise a flexible bag of liquid enteral product, a barbed connector and tubing connecting the flexible bag to the barbed connector. In the illustrated embodiment, the primary fluid passage 22 at the upstream longitudinal end margin includes successive stepped portions 26a, 26b (FIG. 3) having cross-sectional diameters that decrease in size for receiving the barbed connector. The enteral feeding tube 14 is secured within a downstream end margin of the primary fluid passage 22 generally coaxially with the primary section to fluidly connect the primary section 16 to the patient.

Referring to FIGS. 1 and 2, a primary section cap 28 tethered to the primary section 16 by a strap 30 is sized and shaped for removable reception in the upstream end of the primary fluid passage 22 to close the upstream end. The cap 28 includes an annular, elastically deformable rib 32 that is received in an annular, internal groove 34 in the primary fluid passage 22 to releasably secure the cap to the primary section 16.

Referring to FIGS. 1-3, the Y-port 18 is configured to receive, in sealed fluid connection, a male connection component (not shown) from an auxiliary source of liquid enteral product (not shown). For example, the auxiliary fluid passage 24 is configured to receive a catheter tip of a flush syringe. Typically, the outer diameter of a catheter tip is larger than that of an oral tip.

Figure 10:
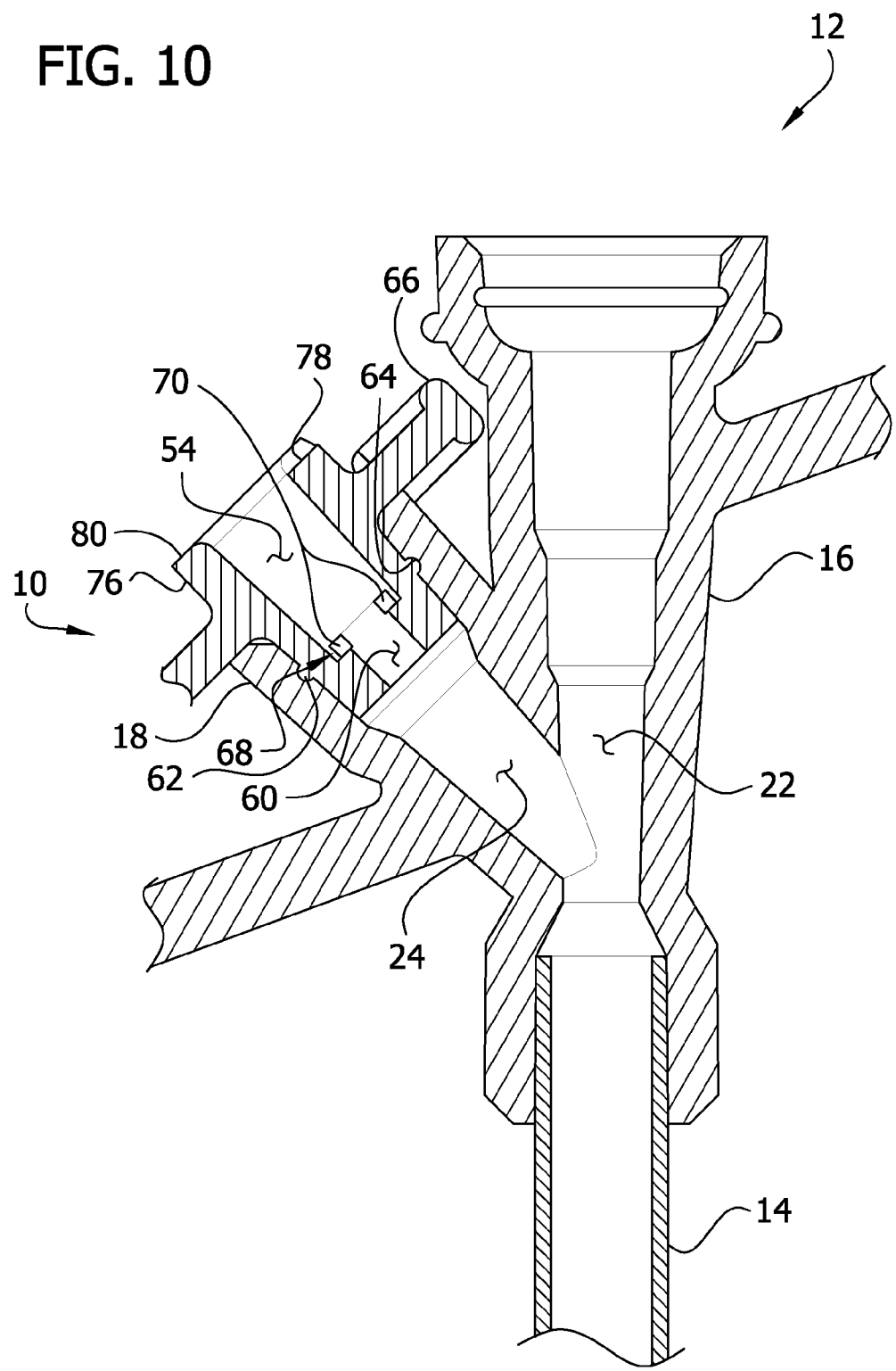
FIG. 10 is an enlarged, fragmentary longitudinal section of the connector assembly and the discriminating oral-tip adaptor as received in a Y-port of the connector assembly.
Figure 11:
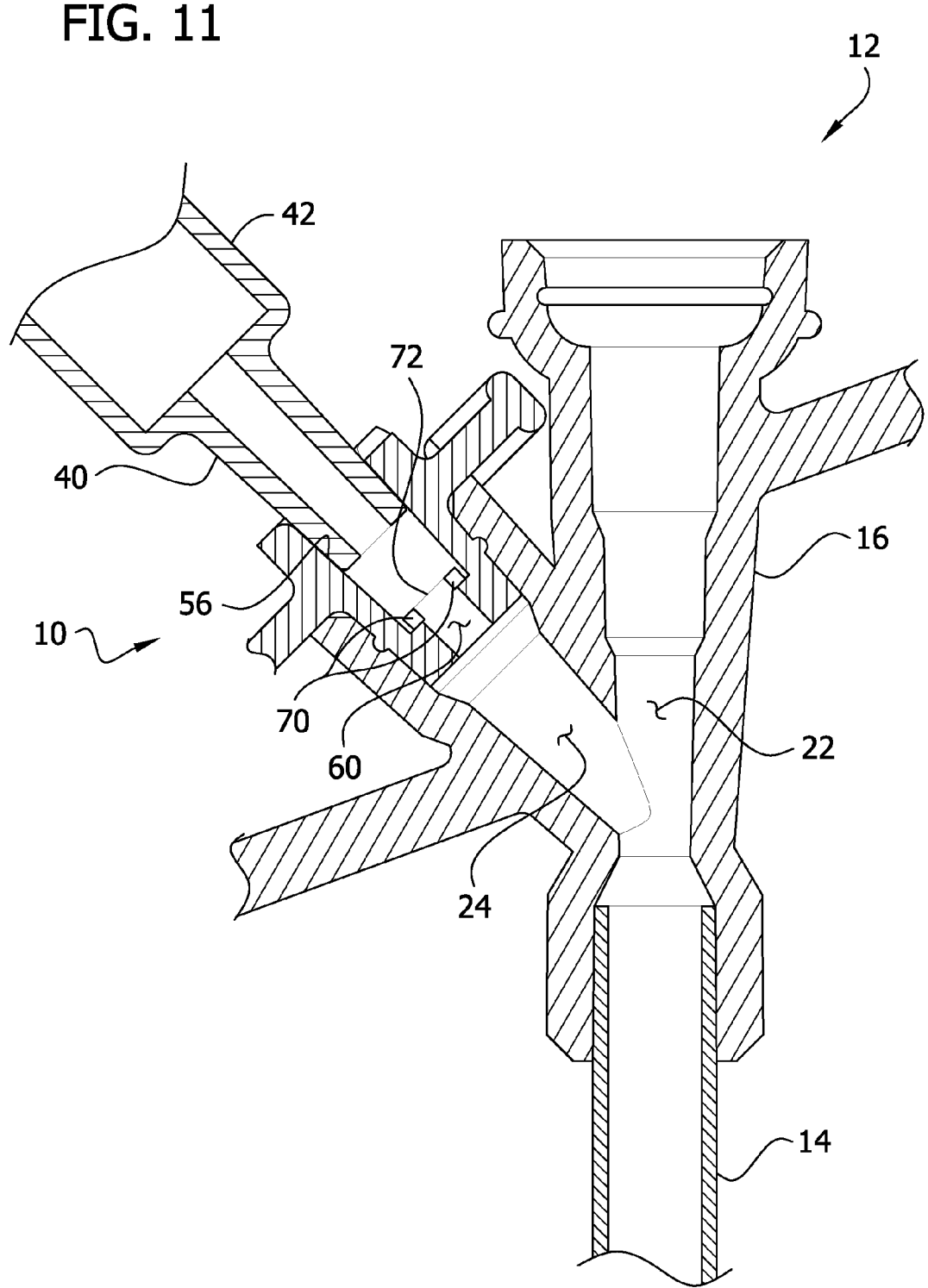
FIG. 11 is similar to FIG. 10 and includes an oral-tip syringe (in section) inserted in the discriminating oral-tip adaptor.

Referring to FIGS. 1, 2 and 4-13, the adaptor 10 of the illustrated embodiment is configured for sealed, releasable connection in the Y-port 18 of the connector assembly 12 to allow sealing connection of an oral tip 40 associated with a first auxiliary delivery device (e.g., an oral-tip syringe 42) to the Y-port to deliver the liquid enteral product through the auxiliary fluid passage and into the feeding tube 14 (FIG. 11). In addition to forming a sealed, fluid connection with the oral tip 40, the adaptor 10 is configured to prevent sealed connection with a standard luer tip 44 of a second auxiliary delivery device 46 (e.g., a luer-slip syringe shown in FIGS. 12 and 12a) and to prevent sealed connection with a standard luer-lock component 48 of a third auxiliary delivery device 50 (e.g. a luer-lock syringe shown in FIG. 13). In this way, only delivery devices (e.g., syringes) having the oral tips are compatible with the adaptor 10. In the illustrated embodiment, the standard luer tip has specifications as given by the International Organization for Standardization (ISO) in ISO 594-1: 1986 and 594-2:1998, including a 6% taper and an outer cross-sectional diameter at the free end of the tip measuring between about 3.925 mm (0.154 in) and about 3.990 mm (0.157 in) for rigid material and between about 3.925 mm (0.154 in) and about 4.027 mm (0.159 in) for semi-rigid material. As also defined herein, the oral tip has an outer cross-sectional diameter that is larger than the cross-sectional diameter of the standard luer tip. Throughout the drawings, the delivery devices are illustrated as syringes because it is envisioned that the adaptor 10 will be used to deliver relatively small amounts of liquid enteral product to the patient. For example, the adaptor 10 may be used when delivering, via the oral-tip syringe 42, medicinal liquid into the feeding tube 14. However, it is understood that the delivery devices may be devices other than syringes.

The adaptor 10 includes a body 52 that is tethered to the Y-port 18 by a strap 53 (FIGS. 1 and 2). The adaptor body 52 has a longitudinal axis L3 (FIG. 4) extending between first and second open ends. A generally cylindrical connection cavity or port 54 for receiving the oral tip 40 in sealed fluid connection (FIGS. 11-13) is defined by an interior wall 56 of the body 52. The connection port 54 extends from the first open end into the body 52. A fluid outlet passage 60 in fluid communication with the connection port 54 extends from the connection port to the second open end of the body 52. As shown in FIG. 10, the second open end of the adaptor body 52 is sized and shaped for reception in the Y-port 18 of the connector assembly 12 so that the fluid outlet passage 60 of the adaptor is in fluid communication with the auxiliary fluid passage 24. An annular rib 62 extending around the adaptor body 52 near the second open end is receivable in an internal, annular groove 64 in the Y-port 18 to releasably connect the adaptor 10 to the Y-port. Both the annular rib 62 and the groove 64 are elastically deformable to allow for releasable connection, although other ways of making the adaptor releasably connectable to the Y-port are within the scope of the present invention. A tab 66 extending outward from the adaptor body 52 may be used by the practitioner to disconnect the adaptor 10 from the Y-port 18 (see, FIG. 4).

Figure 12:
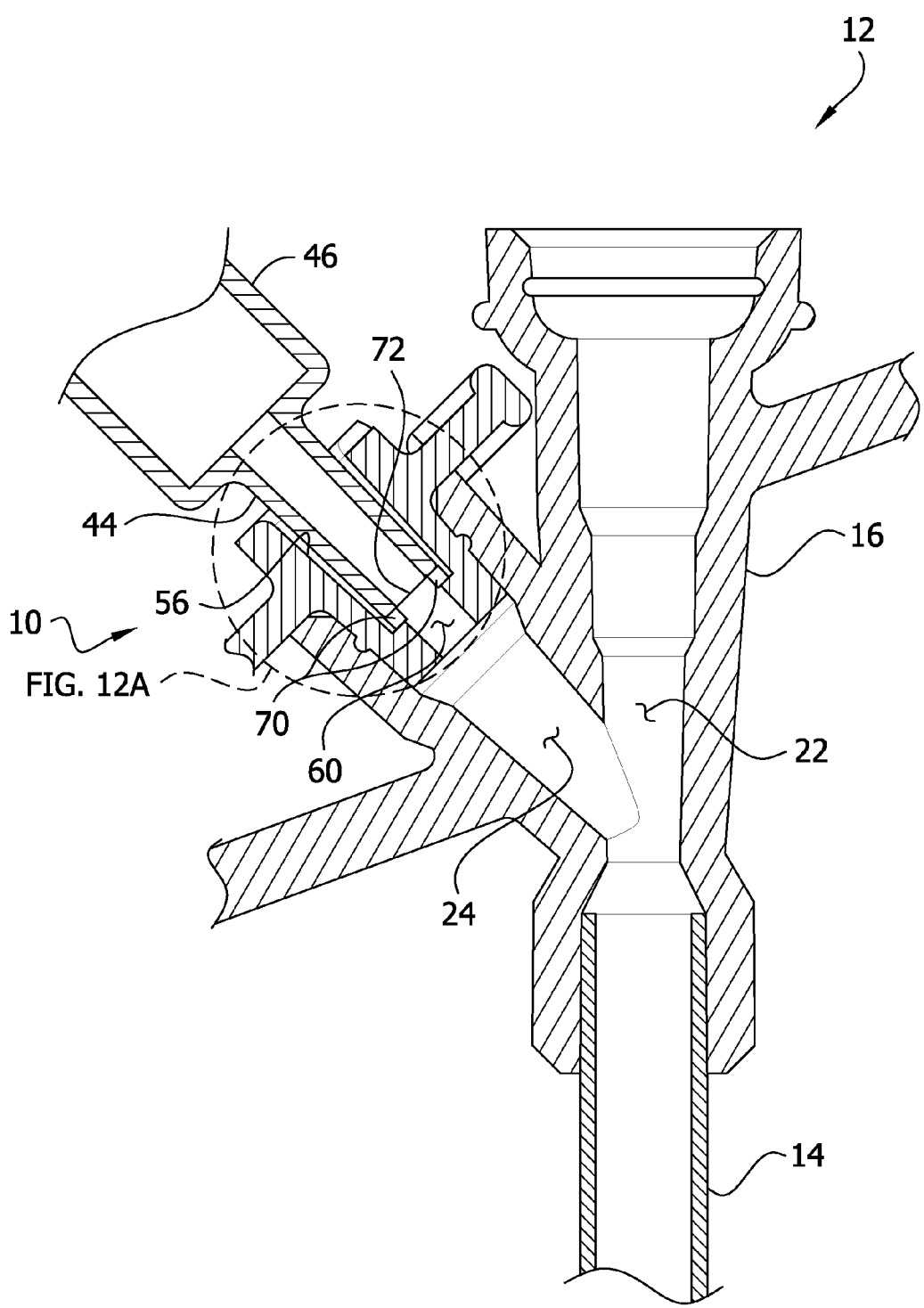
FIG. 12 is similar to FIG. 10 and includes a luer-tip syringe (in section) inserted in the discriminating oral-tip adaptor.

As stated above and as shown in FIG. 11, the connection port 54 is sized and shaped to receive, in sealed fluid connection, the oral tip 40 of the oral-tip syringe 42. In one embodiment, the connection port 54—more specifically the interior wall 56 of the body 52 defining the connection port—is elastically deformable radially (i.e., expansible) with respect to the longitudinal axis L3 of the body 52. In this embodiment, the cross-sectional diameter of the connection port 54 may be smaller than the exterior cross-sectional diameter of the oral tip 44 so that the interior wall 56 defining the connection port elastically deforms and tightly engages the oral tip to form a sealed connection. Referring to FIG. 12, the connection port 54 is also sized and shaped so that the standard luer tip 44 does not seal with the port if the luer tip is inserted into the port. More specifically, the connection port 54 has a cross-sectional diameter that is larger than an external diameter of the standard luer tip 44 so that the luer tip does not sealingly engage the interior wall 56 of the body 52 that defines the port 54.

In the illustrated embodiment, the connection port 54 has a cross-sectional diameter that tapers from the first open end of the adaptor body 52 to the end of the port inside the body 52 to facilitate insertion of the oral tip 40 into the connection port. In one example, the connection port 54 may have a 5 degree taper, a length measuring at least about 7.62 mm (0.300 in), and a cross-sectional diameter measuring between about 4.70 mm (0.185 in) and about 5.21 mm (0.205 in) adjacent to the first open end of the body. The cross-sectional diameter of the connection port 54 at the end of the port inside the body 52 is preferably greater than or equal to about 4.06 mm (0.160 in). The connection port 54 may be of other sizes and shapes within the scope of the present invention. It is understood that only a portion of the oral tip 40 sealingly engaging the interior wall 56 of the adaptor body 42 may be sufficient to form the sealed connection.

Figure 6:
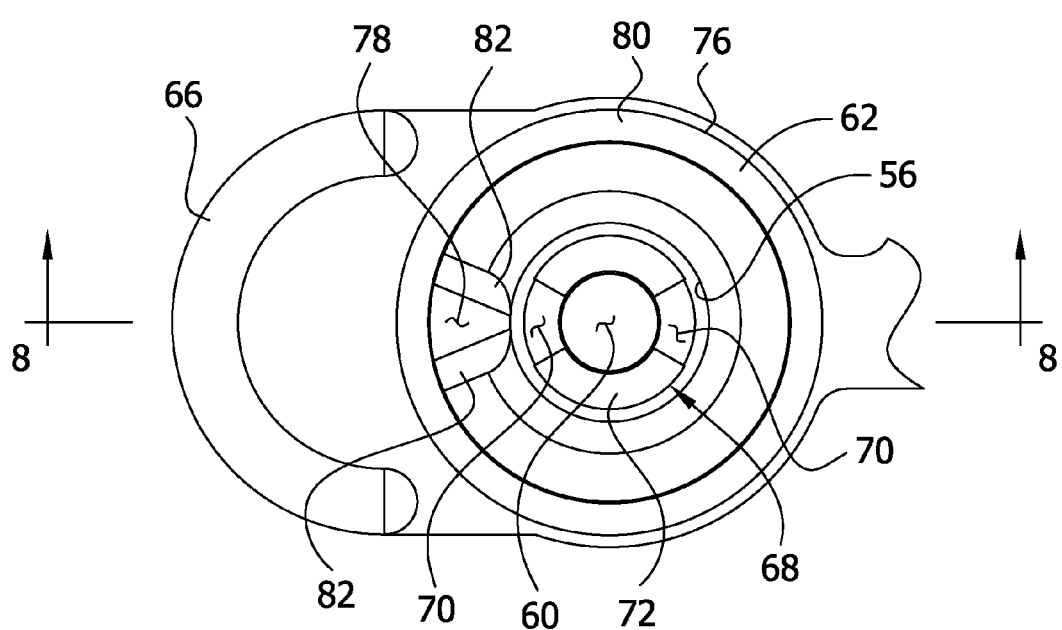
FIG. 6 is a top plan of the discriminating oral-tip adaptor in FIG. 4.
Figure 7:
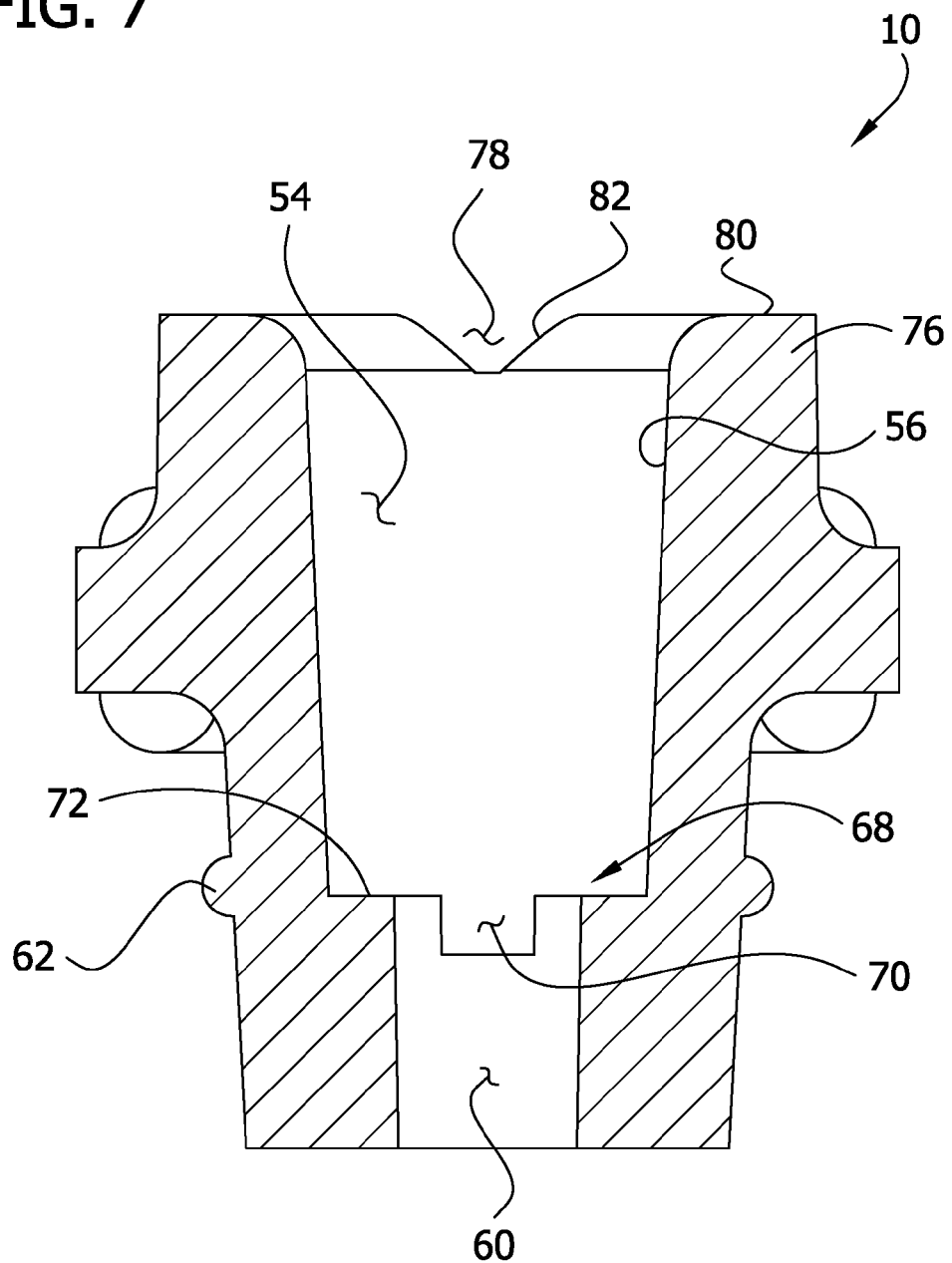
FIG. 7 is a section of the discriminating oral-tip adaptor taken along the line 7-7 in FIG. 5.
Figure 8:
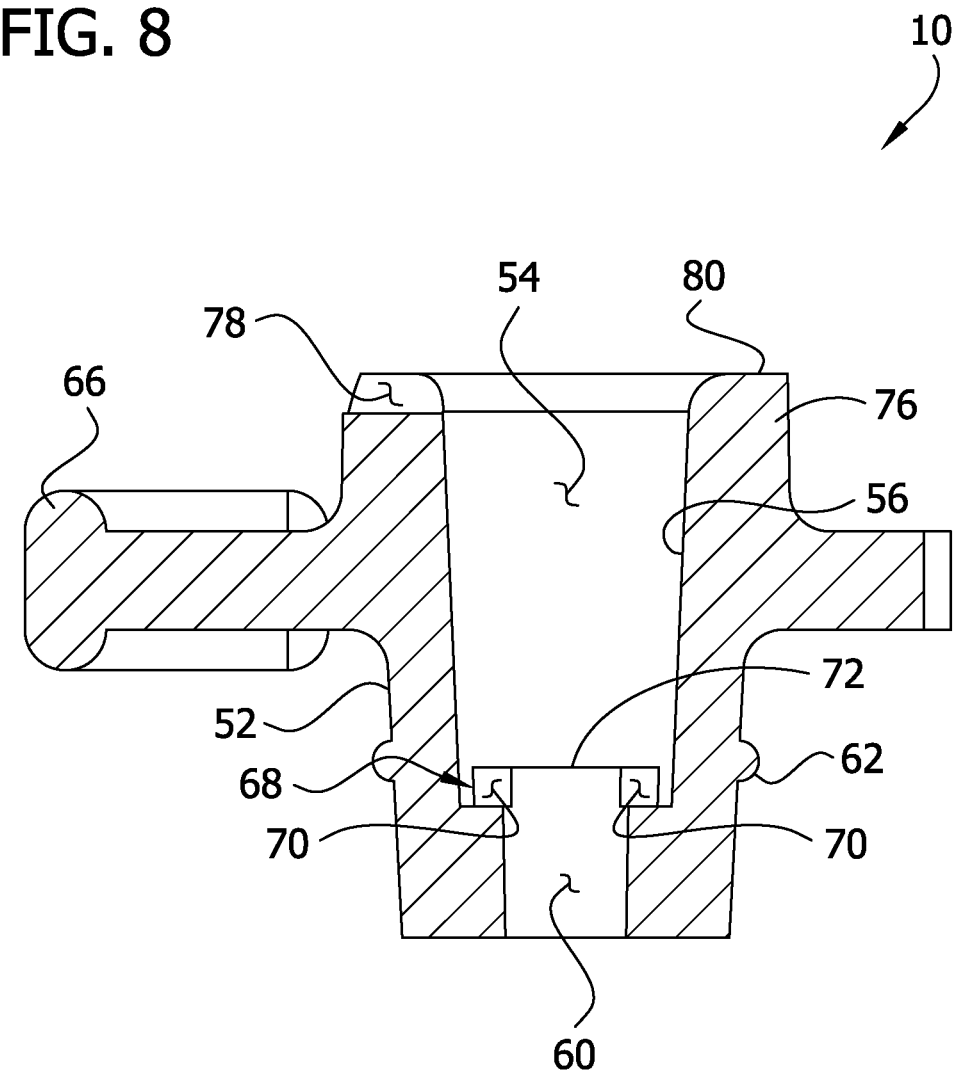
FIG. 8 is a section of the discriminating oral-tip adaptor taken along the line 8-8 in FIG. 6.
Figure 9:
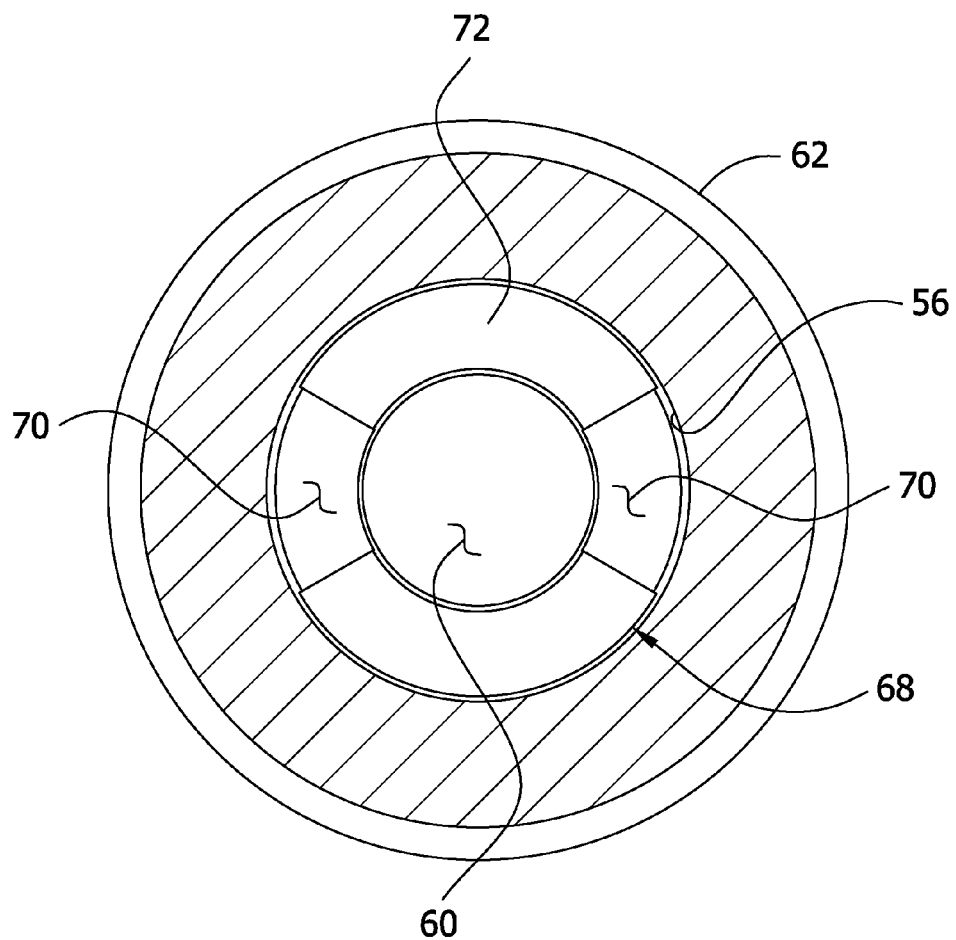
FIG. 9 is an enlarged section of the discriminating oral-tip adaptor taken along the line 9-9 in FIG. 5.

Referring to FIGS. 6-13, the adaptor 10 includes an internal stop, generally indicated at 68, adjacent to the end of the connection port 54 inside the body 52 to further prevent sealed fluid communication between the luer tip 44 and the fluid outlet passage 60. In general, the internal stop 68 is configured so that the luer tip 48 does not form a sealed butt connection with the internal stop when the luer tip is inserted into the connection port 54 and pushed against the stop. In the illustrated embodiment, the internal stop 68 is generally annular defining a central opening between the connection port 54 and the fluid outlet passage 60. Channels 70 are formed in a contact surface 72 of the stop 68 to prevent a sealed butt connection with the luer tip 44. More specifically, a pair of diametrically opposing channels 70 in the surface of the stop 68 extend radially through the stop. The total projected area of the channels 70 in the plane of the contact surface 72 is less than the surface area of the contact surface. The "projected area" is the apparent surface area of the channels as seen in FIG. 6. In the case where the contact surface 72 is not planar, the plane of the contact surface is a best fit plane transverse to the longitudinal axis L3. The width of the channel 70 flares radially outward. In effect and by virtue of the channels 70, the luer tip 44 does not contact the internal stop 68 flush. Other ways of making the surface of the internal stop 68 to prevent sealed contact with the luer tip are within the scope of the invention. It is contemplated that the contact surface 72 may be angled with respect to a transverse plane extending generally transverse to the longitudinal axis of the connection port 54 so that the surface generally slopes downward toward the longitudinal axis of the connection port.

Figure 12A:
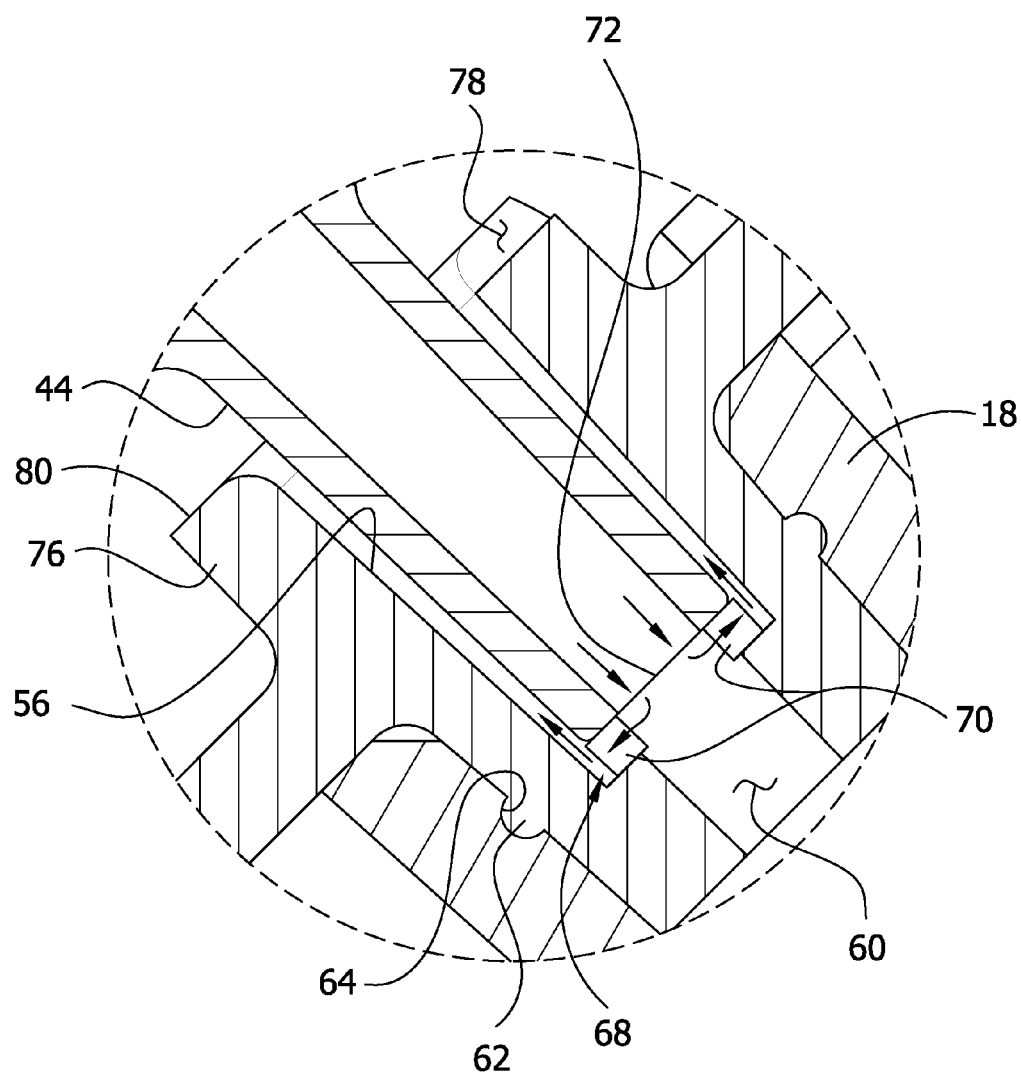
FIG. 12A is an enlarged view of the luer-tip syringe (in section) inserted in the discriminating oral-tip adaptor in FIG. 12.

In use when the luer tip 44 is inserted into the connection port 54 and liquid is delivered into the adaptor 10 from the luer tip, the liquid flows radially outward through the radial channels 70 in the internal stop 68 and up through the connection port through space between the luer tip and the interior wall 56 (see arrows in FIG. 12A). The liquid then leaks out of the adaptor 10 at the first open end to indicate to the user that a sealed connection has not been made. In contrast, when an oral tip 40 is inserted into the connection port 54, the liquid being delivered does not leak out the adaptor 10—even though the oral tip does not form a butt seal with the internal stop 68 and some liquid may flow through the channels 70—because the oral tip is sealed in the connection port and liquid cannot flow between the oral tip and the interior wall 56.

Figure 13:
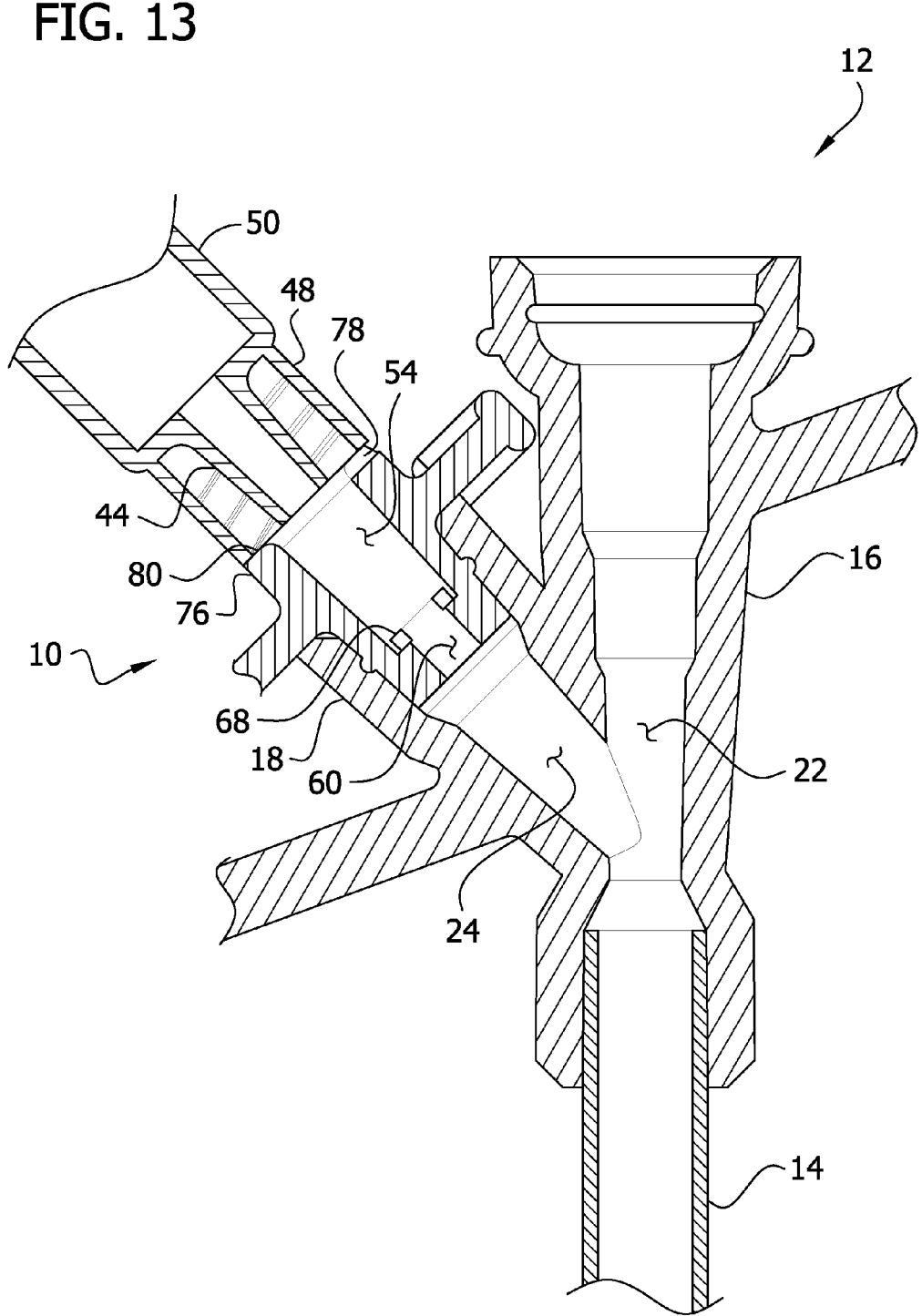
FIG. 13 is similar to FIG. 10 and includes a luer-lock syringe (in section) contacting the discriminating oral-tip adaptor.
Figure 14:
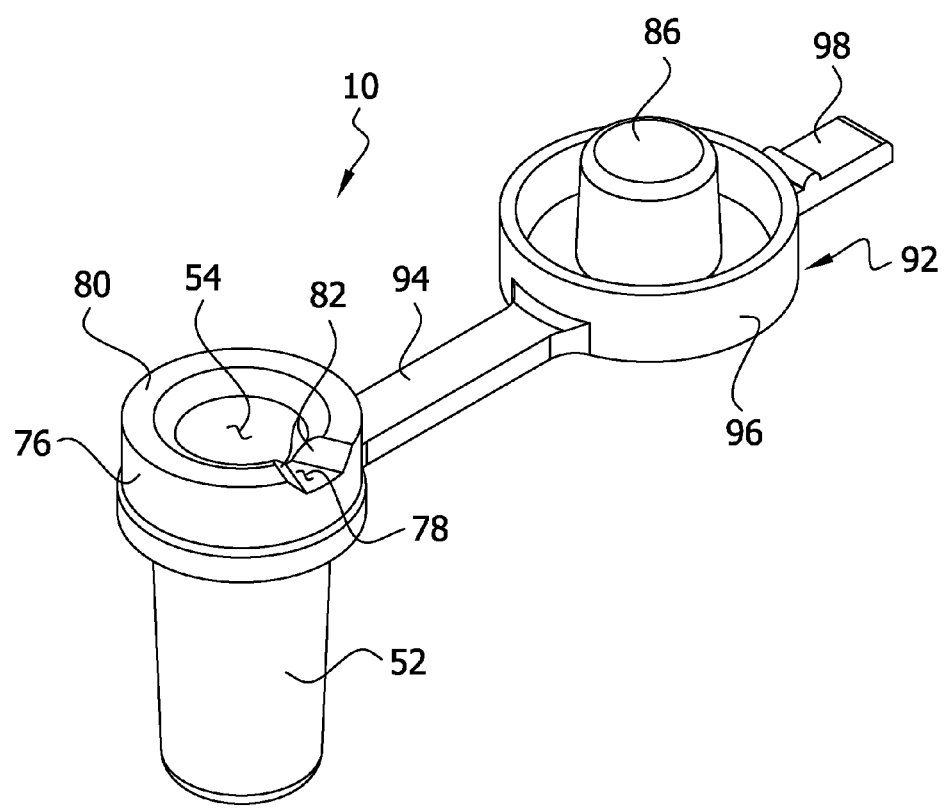
FIG. 14 is a perspective of a second embodiment of the discriminating oral-tip adaptor.
Figure 15:
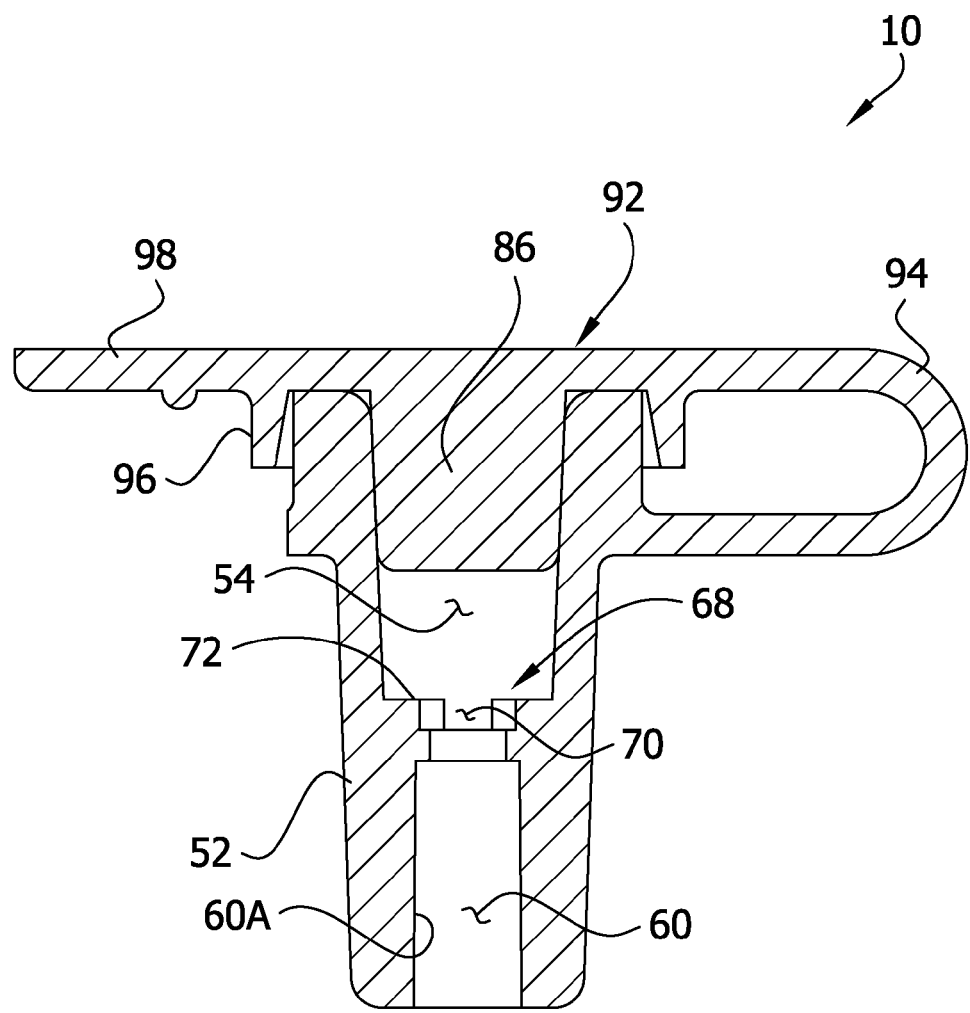
FIG. 15 is an enlarged, longitudinal section of the discriminating oral-tip adaptor in FIG. 14.
Figure 16:
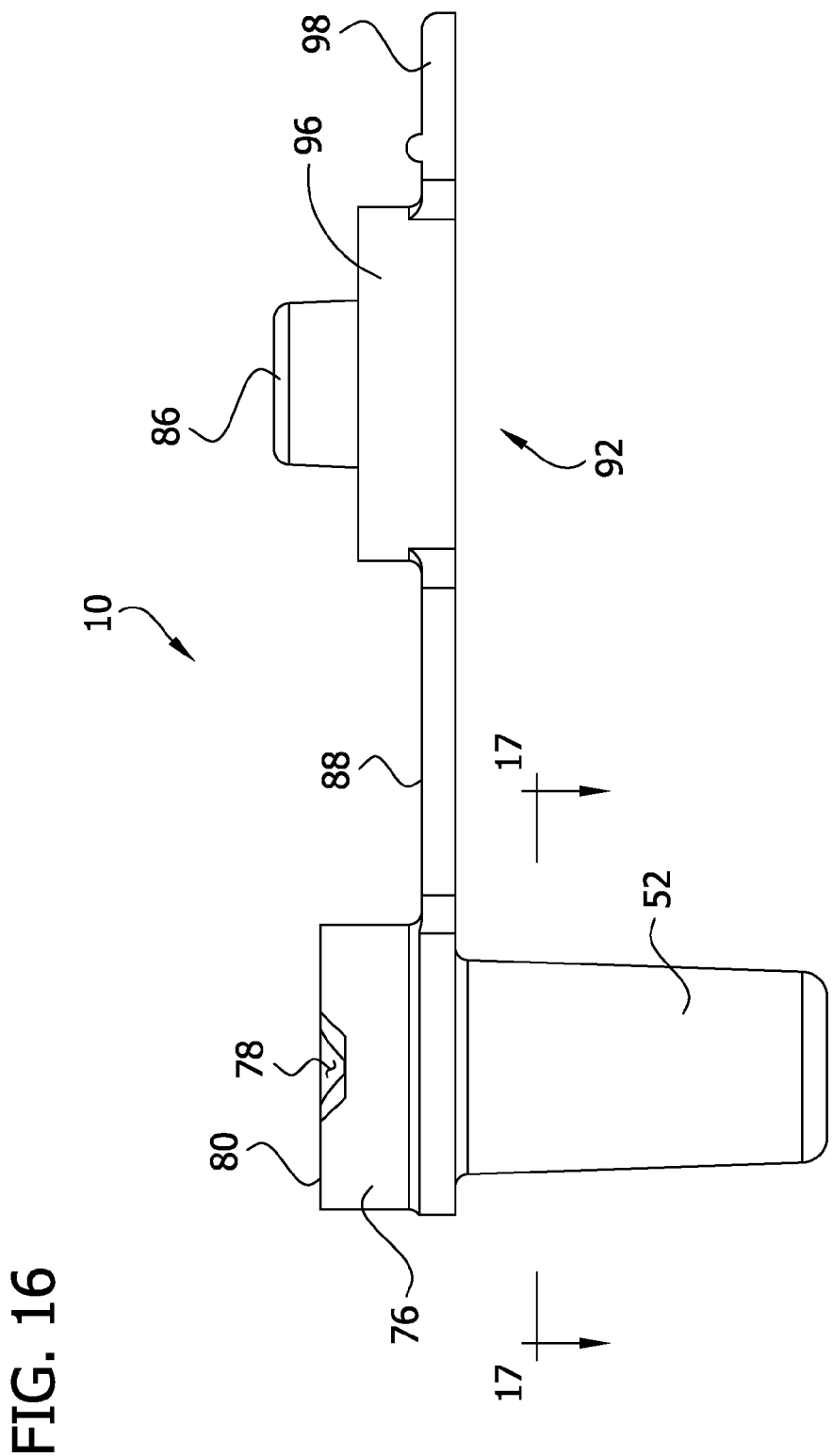
FIG. 16 is a side elevation of the discriminating oral-tip adaptor of FIG. 14.
Figure 17:
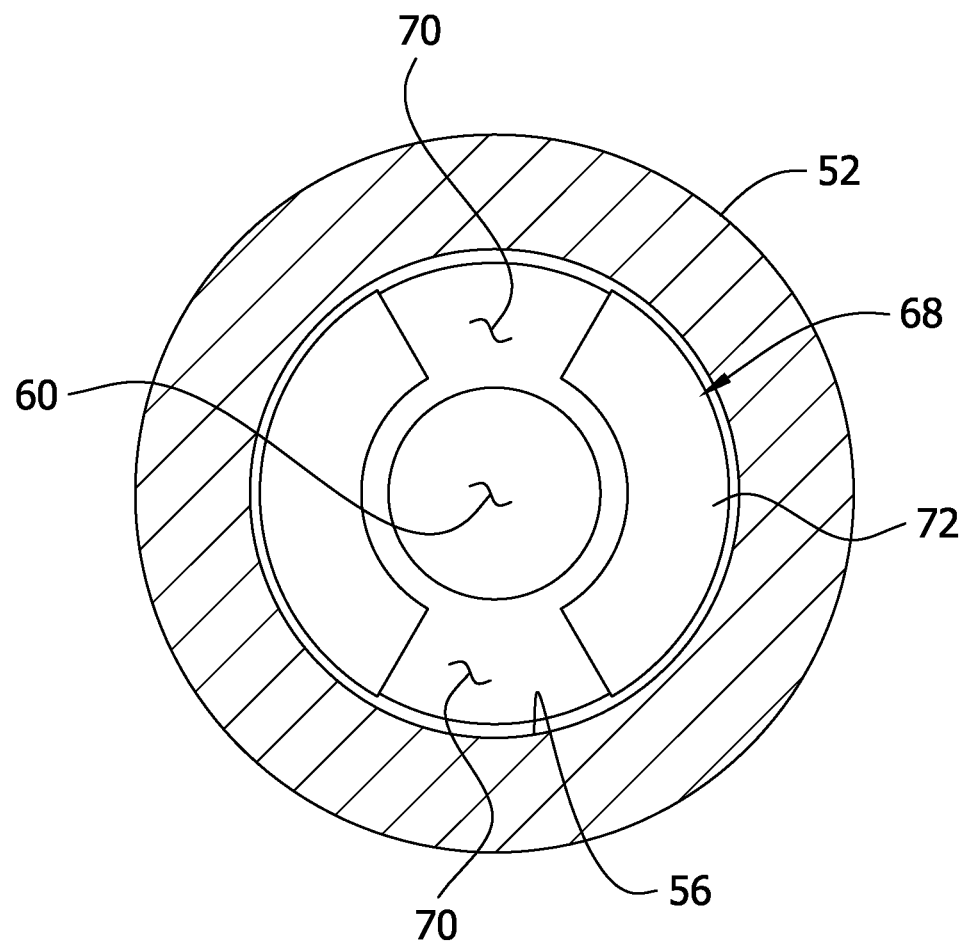
FIG. 17 is a section of the discriminating oral-tip adaptor taken along the line 17-17 in FIG. 16.

Referring to FIGS. 4-8 and 13, the adaptor 10 also includes an external stop 76, generally adjacent to the first open end of the adaptor body 52, to prevent sealed connection between the adaptor body and the luer-lock component or sleeve 48 of the luer-lock syringe 50. In the illustrated embodiment, the external stop 76 is generally annular and surrounds the connection port 54 at the first open end of the adaptor body 52. It is understood that the stop 76 may be other than annular. The stop 76 has an outer diameter that is greater than an internal diameter of the luer-lock sleeve 48 of the luer-lock syringe 50 so that the stop does not fit within the luer-lock sleeve (FIG. 13). In this way, the luer-lock sleeve 48 cannot sealingly connect to the adaptor 10. As an example, the outer diameter of the external stop 76 may measure greater than or equal to about 8.46 mm (0.333 in), and in one embodiment, the outer diameter measures about 8.59 mm (0.338 in). The external stop 76 may have other shapes and sizes within the scope of the present invention.

In addition to preventing a sealed fitted connection with the luer-lock sleeve 44, the external stop 76 is configured to prevent the sleeve from making a sealed butt connection with the stop. In the illustrated embodiment, at least one fluid release channel 78 is formed in a contact surface 80 of the external stop 76 which makes contact with the luer-lock sleeve 48. The release channel 78 extends radially through the external stop 76 with respect to the longitudinal axis L3 from the connection port 54 to outside the adaptor 10. The projected area of the release channel 78 in the plane of the contact surface 80 of the external stop 76 (as seen in FIG. 6) is less than the surface area of the contact surface. The width of the channel 78 flares radially outward. In effect, the release channel 78 ensures that liquid will escape (i.e., leak) out the connection port 54 when the luer-lock sleeve 48 is used. Otherwise, if the luer-lock sleeve 48 could make a sealed butt connection with the external stop 76, which would prevent the liquid from flowing out of the connection port 54. In the illustrated embodiment, the release channel 78 flares radially outward and has beveled side walls 82 (FIG. 4) extending downward from the contact surface 80. Other ways of providing a fluid release passage in fluid communication with the connection port 54, including projections extending outward from the surface of the stop 76, are within the scope of the invention. It is also contemplated that an opening may be formed at other locations other than the contact surface 80 of the external stop 76. For example and as described more fully in relation to later embodiments herein, a passage may extend radially through adaptor body 52 from the connection port 54.

Referring to FIGS. 1 and 2, the connector assembly 12 further includes an adaptor plug 86 tethered by a strap 88 to the strap 53 that tethers the adaptor 10 to the Y-port 18. The plug 86 is sized and shaped for insertion in the connection port 54 to close the port.

The connector assembly 12 of the illustrated embodiment may be formed as a one-piece, integral structure. As an example, the connector assembly 12 may be formed by injection molding using an elastically deformable plastic, such as PVC with a durometer of between about 70 and about 85, although the connector assembly may have other hardness and may be made of other material such as other thermoplastic elastomers, such as polypropylene or polycarbonate or urethanes, or thermal set material, such as silicone or rubber. Alternatively, one or more of the components of the connector assembly 12 may be formed separately. The adaptor 10 may be deformable to allow for variations in the size of the oral tip 40.

Referring to FIGS. 14-17, the second embodiment of the discriminating fluid adaptor is indicated generally at 10. This embodiment is similar to the embodiment illustrated in FIGS. 1-13, and therefore, like components are indicated by corresponding reference numbers. The present adaptor 10 is different than the first embodiment in that the present adaptor is directly secured to the feeding tube 14 and is not part of a connector assembly. Like the first embodiment, the present adaptor 10 includes the connection port 54, the fluid outlet passage 60, the internal stop 68 with the radial channels 70, and the external stop 76 with the radial channel 78. The fluid outlet passage 60 has a tube-connection portion 60A in which the feeding tube 14 is secured. The adaptor 10 also includes an adaptor cap, generally indicated at 92, tethered to the adaptor by a strap 94. The adaptor cap 92 includes the adaptor plug 86 (similar to the plug in the first embodiment) and a skirt 96 surrounding the plug for being received on the adaptor. A tab 98 extends outward from the cap 92 for removing the cap from the adaptor 10.

Figure 18:
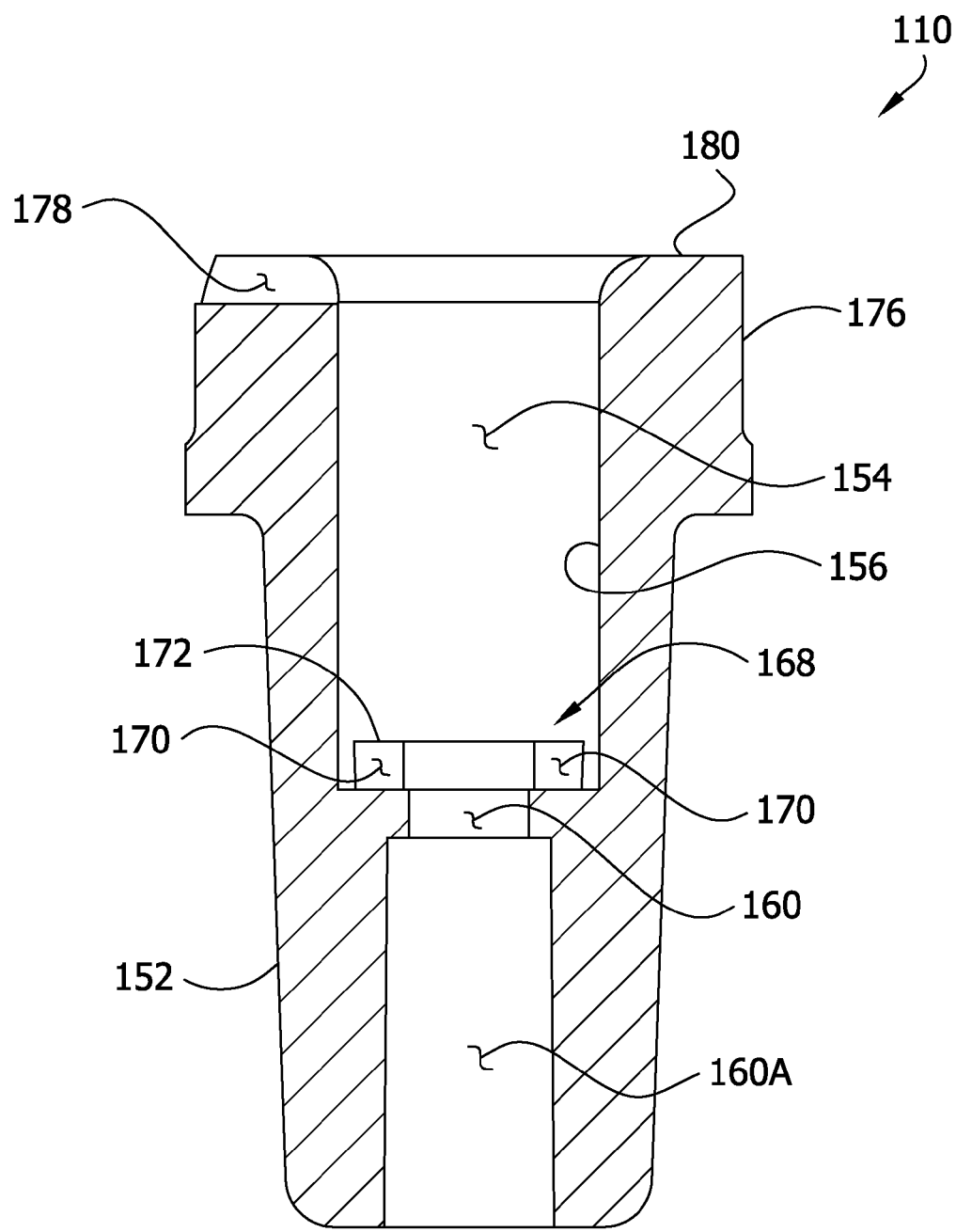
FIG. 18 is a section of a third embodiment of the discriminating oral-tip adaptor.

Referring to FIG. 18, a third embodiment of the adaptor is generally indicated at 110. This embodiment is similar to the second embodiment illustrated in FIGS. 14-17, and therefore, like components are indicated by corresponding reference numbers plus 100 (e.g. channels 170 and contact surface 172). The difference between the second embodiment and the present adaptor 110 is that unlike the tapered connection port 54 in the second embodiment, the connection port 154 in the present adaptor has a substantially uniform cross section. In other words, the connection port 154 has cross-sectional diameter that is uniform from generally adjacent the first open end of the adaptor body 152 to the end of the port inside the body. The diameter of the connection port 154 provides a sealed connection with the oral tip 40 and prevents a sealed connection with the standard luer tip 44. For example, the connection port 154 might in one embodiment have a uniform diameter along its length measuring between about 4.19 mm (0.165 in) and about 5.08 mm (0.200 in), and preferably about 4.45 mm (0.175 in). Other features of the two embodiments are substantially the same.

Figure 19:
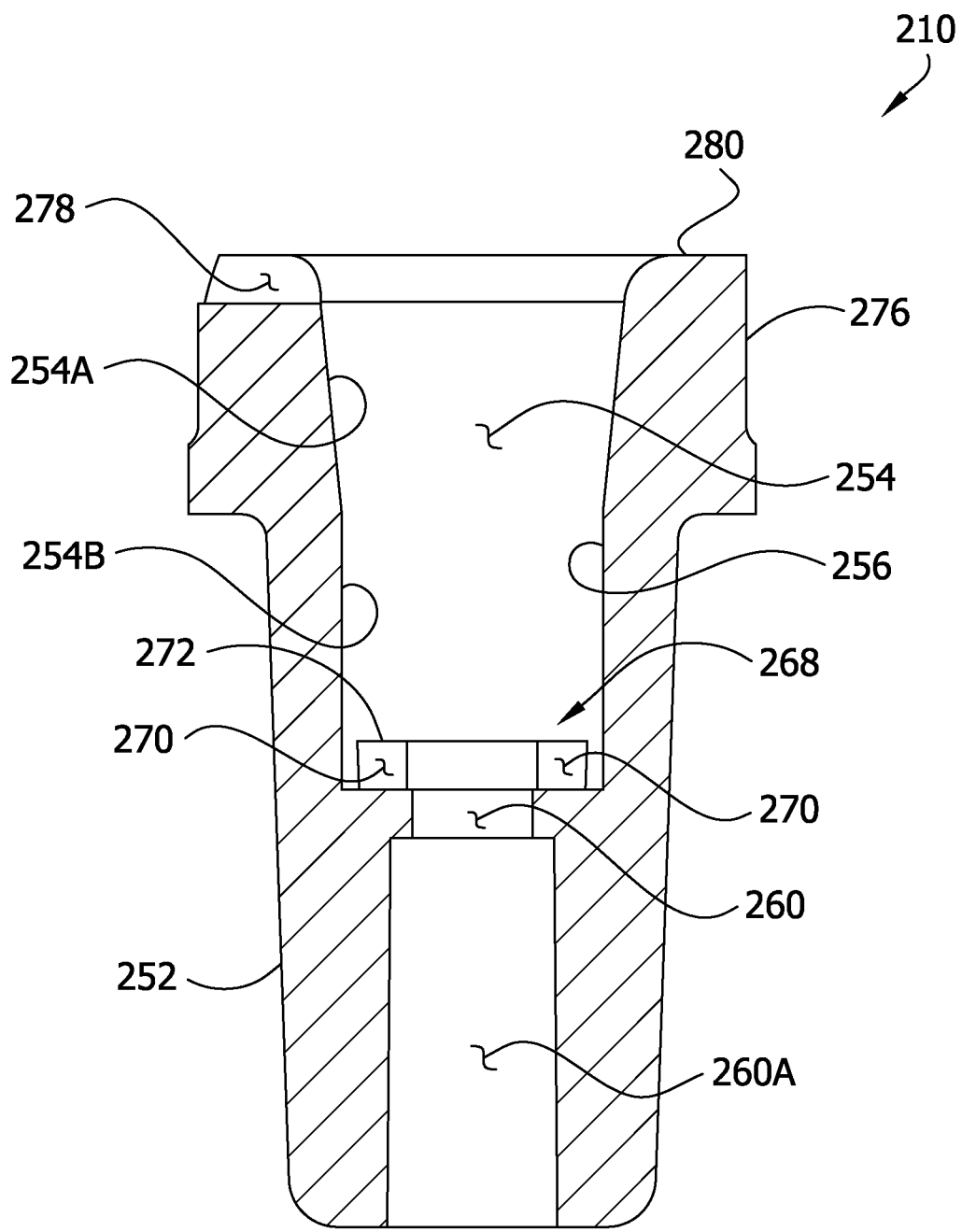
FIG. 19 is a section of a fourth embodiment of the discriminating oral-tip adaptor.

Referring to FIG. 19, a fourth embodiment of the adaptor is generally indicated at 210. This embodiment is similar to the second embodiment illustrated in FIGS. 14-17, and therefore, like components are indicated by corresponding reference numbers plus 200. The difference between the second embodiment is the present adaptor 210 is that only an upper portion 254A of the connection port 254 in the present adaptor is tapered along its length, while a lower portion 254B has a constant diameter. More specifically, the upper portion 254A of the connection port 254 has cross-sectional diameter that tapers from adjacent the first open end of the adaptor body 252 to an intermediate location between the first open end and the end of the port inside the body. The cross-sectional diameter of the lower portion 254B of the connection port 254 is substantially uniform from the intermediate location to the end of the port inside the body 252. Liquid delivered via the standard luer tip will leak out the first open end of the adaptor body 252 because the standard luer tip 40 does not seal with the interior wall 256 defining the connection port 254. Moreover, liquid delivered via the oral tip will not leak out the first open end of the adaptor body 252 because the oral tip 40 seals with the interior wall 256 defining the connection port 254. As an example, the upper portion 254A might have a 5 degree taper, a length measuring at least about 7.62 mm (0.300 in), and a cross-sectional diameter tapering between about 4.70 mm (0.185 in) and about 5.21 mm (0.205 in) adjacent to the first open end of the body to greater than or equal to about 4.06 mm (0.160 in) at the intermediate location. The lower portion 254B may have a cross-sectional diameter of greater than or equal to about 4.06 mm (0.160 in) and a length of greater than or equal to about 5.08 mm (0.200 in).

Figure 20:
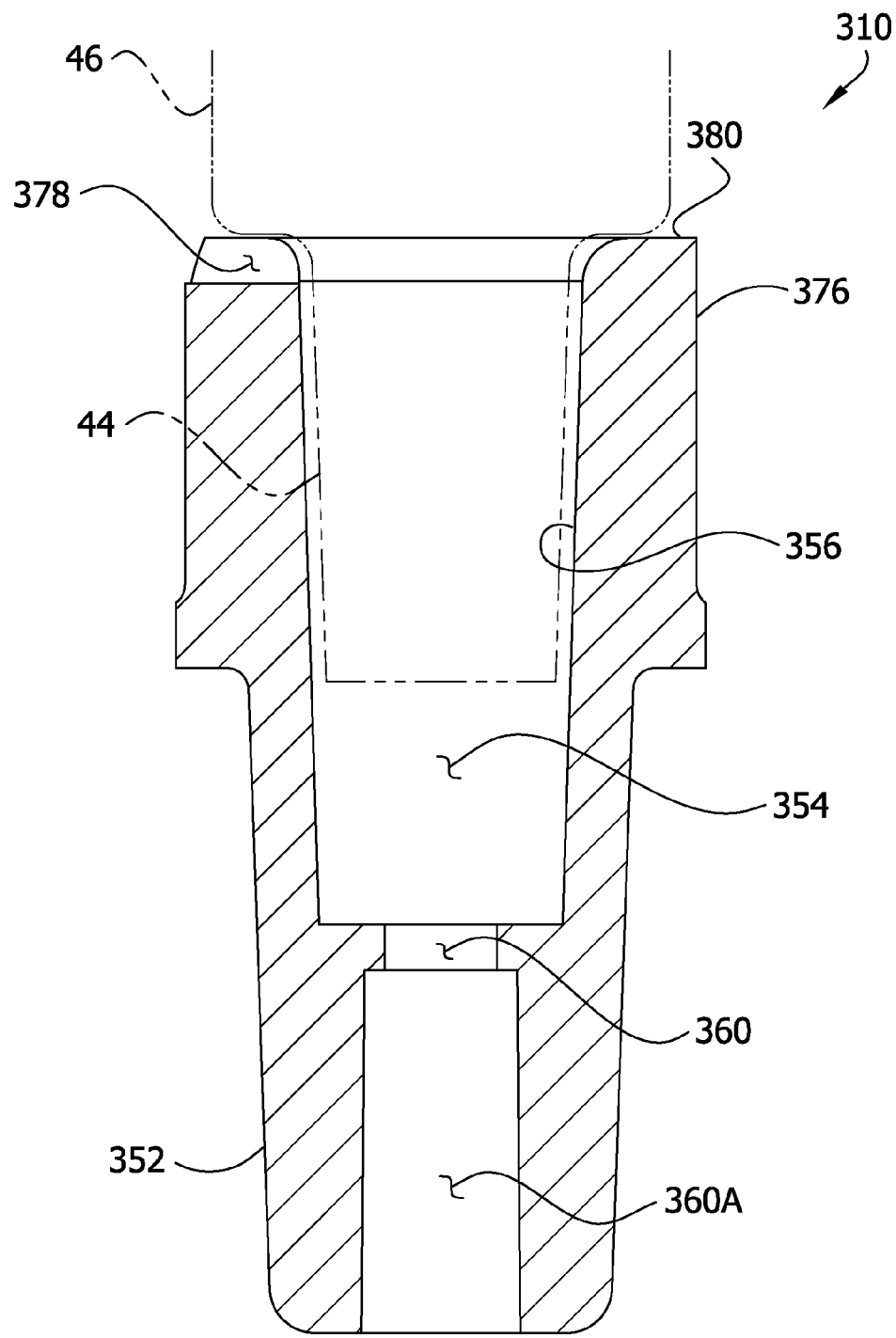
FIG. 20 is a section of a fifth embodiment of the discriminating oral-tip adaptor.

Referring to FIG. 20, a fifth embodiment of the adaptor is generally indicated at 310. This embodiment is similar to the second embodiment illustrated in FIGS. 14-17, and therefore, like components are indicated by corresponding reference numbers plus 300. The difference between the second embodiment and the present adaptor 310 is that the connection port 354 in the present adaptor has a length extending from the first open end to the end inside the body 352 that is sufficient to prevent the standard luer tip 44 from contacting the end of the connection port inside the body. The barrel of the syringe engages a contact surface 380 of an external stop 376 preventing bottoming of the luer tip 44. Moreover, the adaptor 310 does not have an internal stop because the length of the connection port 354 prevents a sealed connection between the standard luer tip 44 and the end of the port 354 inside the body 352. As such, liquid delivered via the standard luer tip will leak out the first open end of the adaptor body 352 because the standard luer tip 40 does not seal with the interior wall 356 defining the connection port 354 and, as shown in FIG. 20, the release channel(s) 378 provide a clearance to allow liquid to flow out the connection port when the barrel of the syringe engages the contact surface 380 of the external stop 376. Moreover, liquid delivered via the oral tip will not leak out the first open end of the adaptor body 352 because the oral tip 40 seals with the interior wall 356 defining the connection port 354. As an example, the connection port 354 may have a length greater than about 12.70 mm (0.500 in). Although the connection port 354 may be of other lengths within the scope of the invention, it is believed that each of the lengths in the above range is of sufficient magnitude to prevent most, if not all, types and brands of standard luer tips that are presently on the market from contacting the end of the port 254 inside the body 252. However, because the standard luer tip 44 does not have a standardized length under ISO 594-1 and 594-2, it is contemplated that the adaptor 310 may include the internal stop to provide an additional safeguard should a present or future type or brand of standard luer tip 44 have a length sufficient to contact the end of the port 354 inside the body 352.

Figure 21:
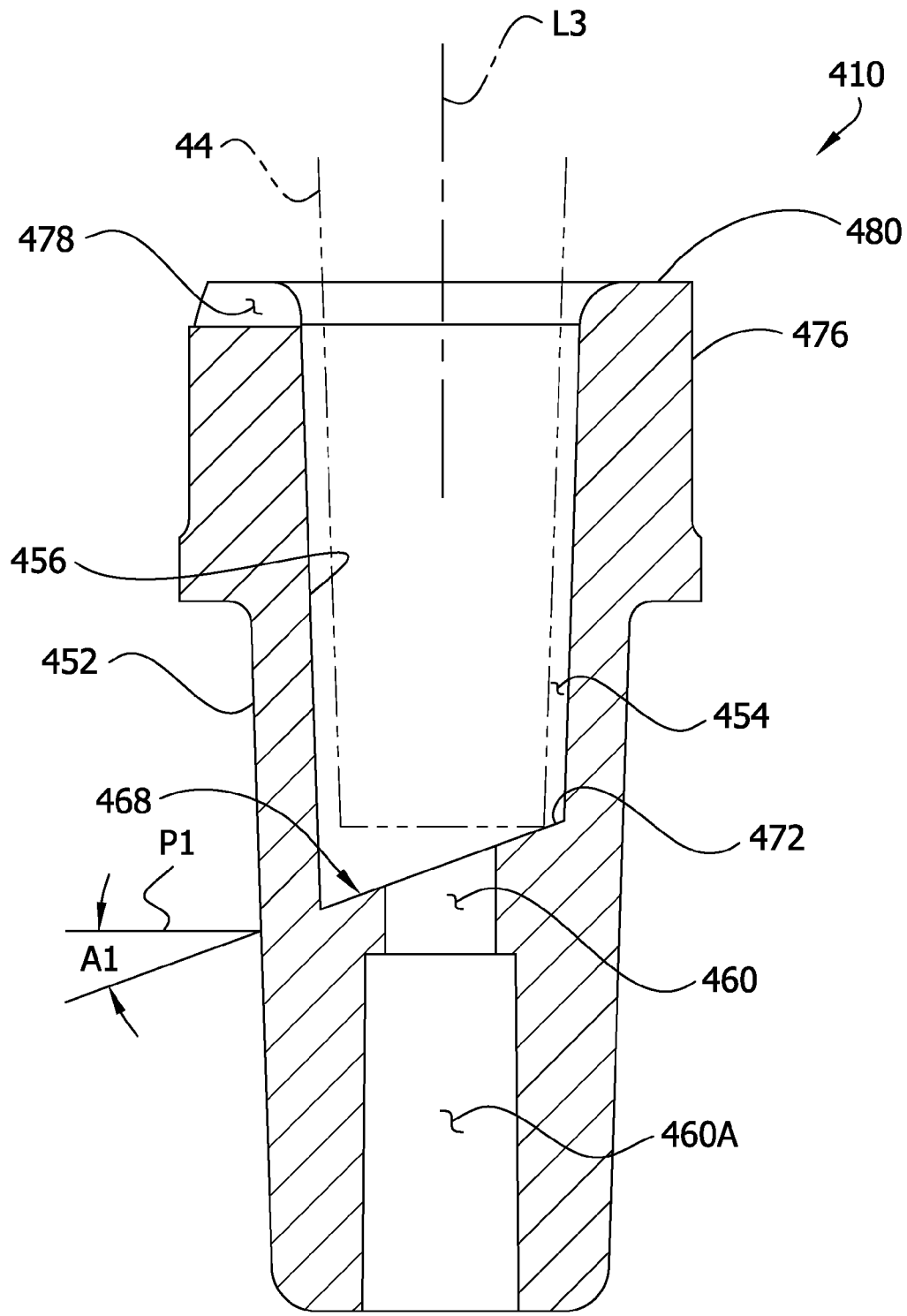
FIG. 21 is a section of a sixth embodiment of the discriminating oral-tip adaptor, also showing a syringe tip in phantom.

Referring to FIG. 21, a sixth embodiment of the adaptor is generally indicated at 410. This embodiment is similar to the second embodiment, and therefore, like components are indicated by corresponding reference numbers plus 400. The difference between the second embodiment and the present adaptor 410 is that the contact surface 472 of the internal stop 468 of the present adaptor 410 is coextensive with the end of the port 254 inside the body 252. The stop 468 does not include channels, but instead, the contact surface 472 extends at an angle A1 with respect to a transverse plane P1 extending generally transverse to the longitudinal axis L3 of the port 454. The standard luer tip 44 does not make flush contact with the angled contact surface 472 when the component is inserted into the connection port 254. As shown in FIG. 21, only part of the free end of the standard luer tip 44 contacts a portion of the angled contact surface 472 (even if the luer tip is canted within the port) leaving a gap between the remaining part of the end of the standard luer tip and a remainder of the contact surface. Thus, liquid delivered via the standard luer tip 44 will leak out the first open end of the adaptor body 452 because the standard luer tip does not seal with the interior wall 456 defining the connection port 454. Liquid delivered via the oral tip 40 does not leak out the first open end of the adaptor body 452 because the oral tip seals with the interior wall 456 defining the connection port 454. As an example, the angle A1 may measure between about 5 degrees and about 30 degrees with respect to the transverse plane, more preferably, between about 10 degrees and about 20 degrees, and more preferably between about 10 degrees and 15 degrees.

In another embodiment, internal stop 480 extends at angle A1 with respect to plane P1. Internal stop 468 can be configured as described above or can be lowered beyond any expected contact with a luer tip, such as shown in FIG. 20. This is another example of how features described herein can be "mixed and matched" as desired to defeat sealing engagement of an IV luer tip according to the present invention.

Figure 22:
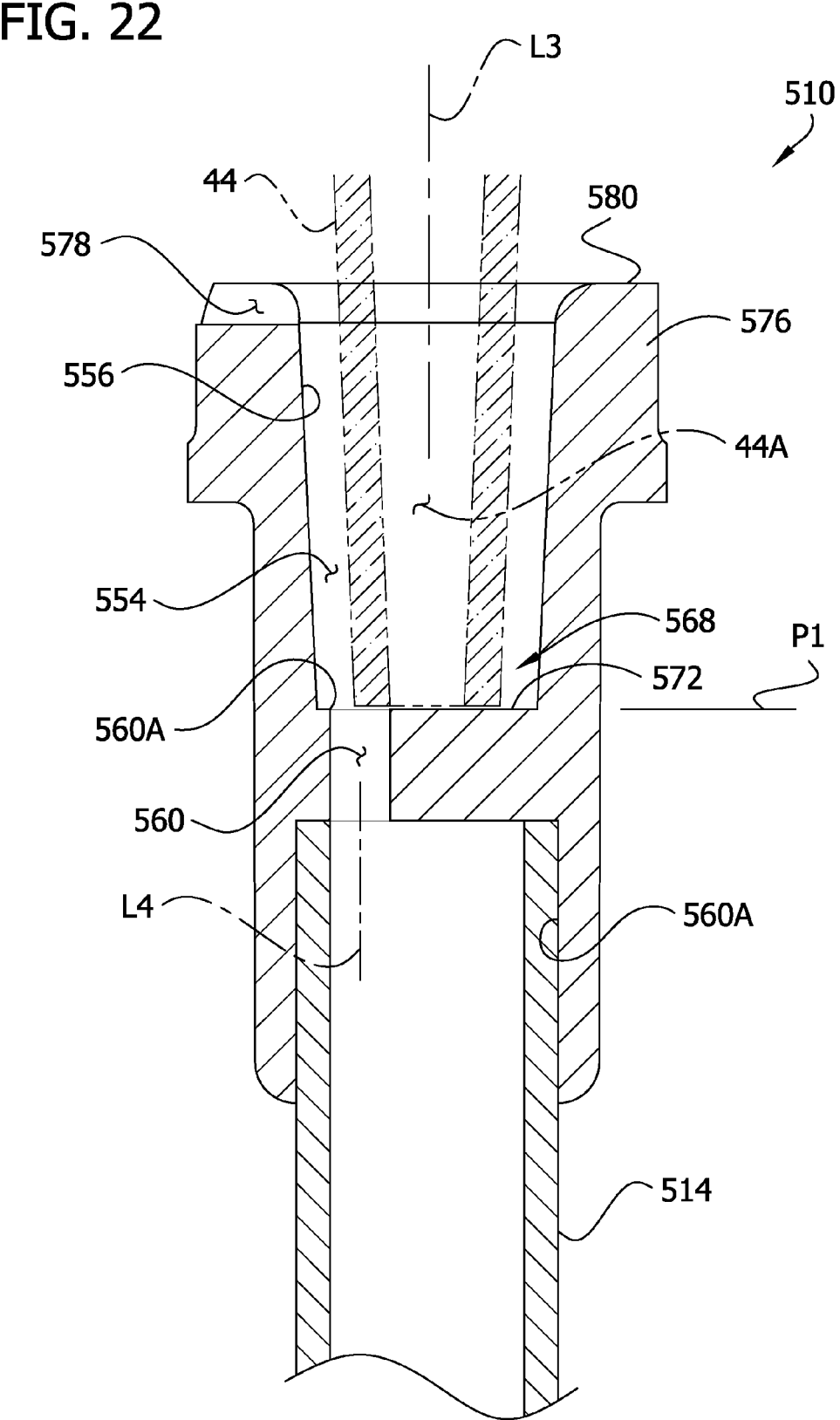
FIG. 22 is a section of a seventh embodiment of the discriminating oral-tip adaptor.

Referring to FIG. 22, a seventh embodiment of the adaptor is generally indicated at 510. This embodiment is similar to the sixth embodiment illustrated in FIG. 21, and therefore, like components are indicated by corresponding reference numbers plus 100. The difference between the sixth embodiment and the adaptor 510 is that contact surface 572, which is coextensive with the internal stop 568, is not angled but is coplanar with the transverse plane P1. Moreover, an opening 560A of the outlet passage 560 adjacent to the end of the connection port 554 is not aligned with the longitudinal axis L3 of the connection port. Instead, the opening 560A of the outlet passage 560 is offset with respect to the longitudinal axis L3 of the connection port 554 so that when the standard luer tip 44 is inserted into the port, a fluid passage 44A of the luer tip is either not in fluid communication with the outlet passage opening or only partially in fluid communication with the opening. In any event, the luer tip 44 is unable to seal entirely around the opening 560A so that a path of the port 554 around the luer tip always remains open. In contrast, when the oral tip (not shown) is inserted into the connection port 554, the oral tip seals with interior wall 456 before it contacts the contact surface 572 so that the oral tip is spaced longitudinally from the stop in fluid communication with the outlet passage. Thus, liquid delivered via the standard luer tip will leak out the first open end of the adaptor body 552 because the standard luer tip 40 cannot seal with the interior wall 556 defining the connection port 554, while liquid delivered via the oral tip 40 does not leak out the first open end of the adaptor body 552 because the oral tip seals with the interior wall 556 around its entire circumference.

In the illustrated embodiment, an upstream portion of the outlet passage 560 between the connection port 554 and the tube-connection portion 560A has a longitudinal axis L4 that is generally parallel to the longitudinal axis L3 of the connection port 554. It is contemplated that the outlet passage 560 may be formed so that the longitudinal axis L4 of the upstream portion of the outlet passage angles toward the longitudinal axis L3 of the connection port 554 away from the opening 560A.

Figure 23:
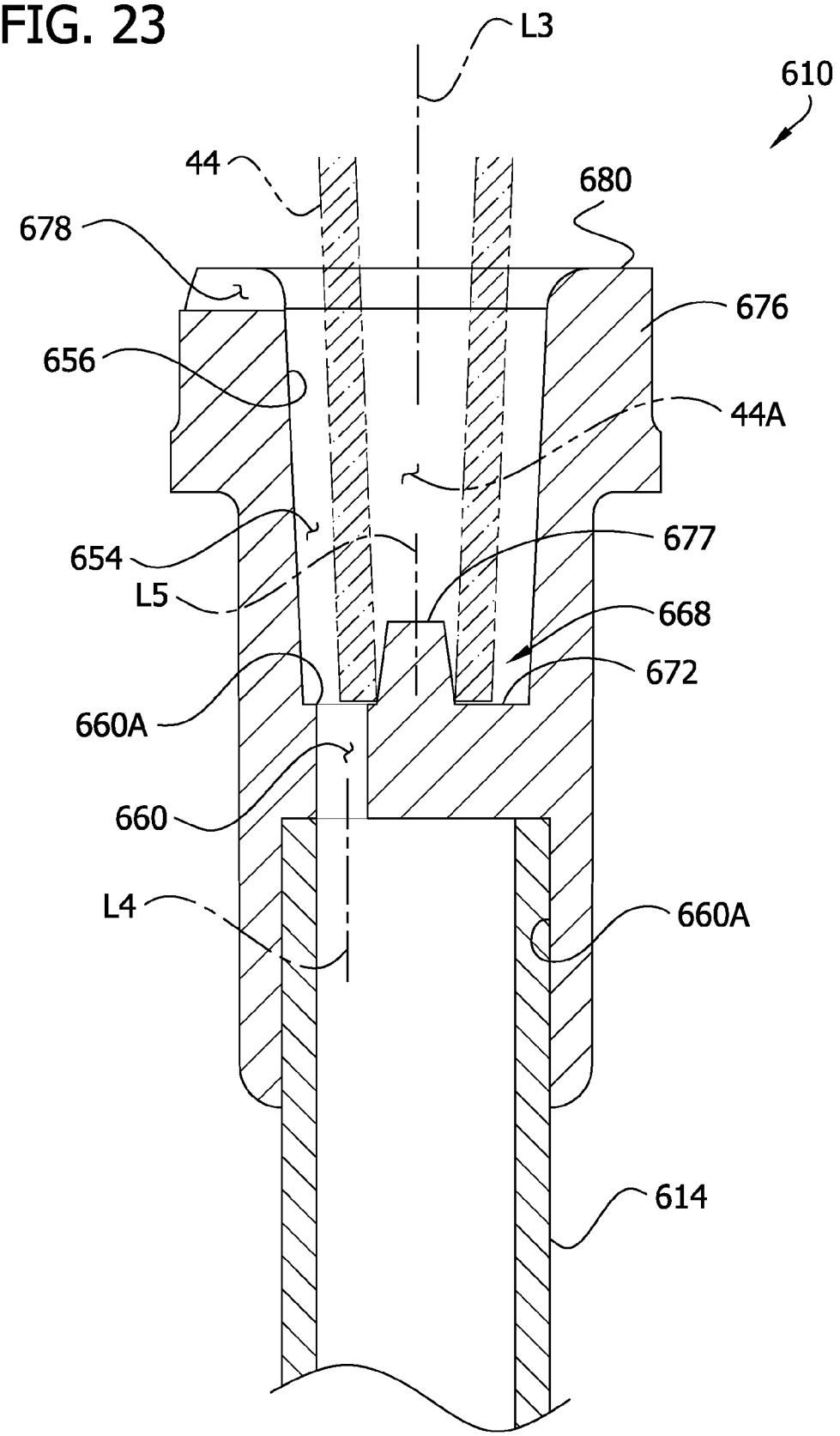
FIG. 23 is a section of an eighth embodiment of the discriminating oral-tip adaptor.

Referring to FIG. 23, an eighth embodiment of the adaptor is generally indicated at 610. This embodiment is similar to the seventh embodiment, and therefore, like components are indicated by corresponding reference numbers plus 100. The difference between the seventh embodiment and the adaptor 610 is that the present adaptor additionally includes a frustoconical plug 677 on the contact surface 672 of the internal stop 668 projecting toward the first open end of the adaptor body 652. The plug 677 has a longitudinal axis L5 that is generally aligned with the longitudinal axis L3 of the connection port 654. As shown in FIG. 23, the plug 677 is sized and shaped for reception in the fluid passage 44A of the luer tip 44 when the luer tip is inserted into the connection port 654. The tapered shape of the frustoconical plug 677 guides the plug into the fluid passage 44A upon insertion of the luer tip 44 into the connection port 654. The plug 677 prevents liquid from being delivered via the standard luer tip. Preferably, the connection port 654 is sized and shaped so that the oral tip (not shown)_seals with the interior wall 656 defining the connection port 654 at a location spaced from (i.e., above) the plug 677. In this way, the plug 677 does not enter the oral tip when the component is inserted into the connection port 654.

Figure 24:
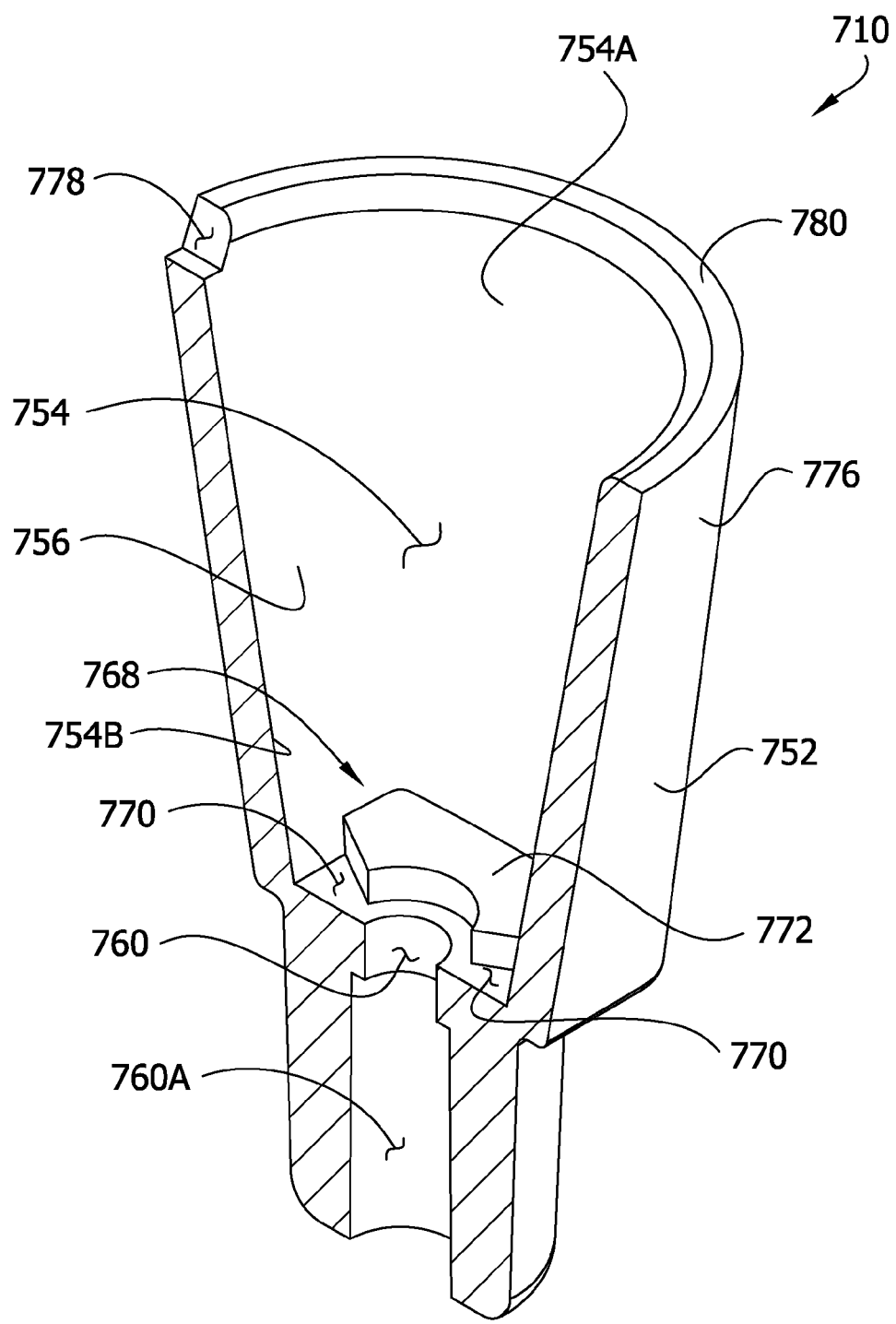
FIG. 24 is a perspective of a section of a ninth embodiment of the discriminating oral-tip adaptor.

Referring to FIGS. 24 and 24A, a ninth embodiment of the adaptor is generally indicated at 710. This embodiment is similar to the second embodiment, and therefore, like components are indicated by corresponding reference numbers plus 700. The difference between the second embodiment and the present adaptor 710 is that the connection port 754 of the present adaptor has a cross section that transitions from being generally circular or elliptical at the first open end of the adaptor body 752 to being convex polygonal (e.g., square-shaped or rectangular) at the end of the port inside the adaptor body. This, an upper portion 754A of the connection port 754 has a circular cross section and a lower portion 754B has a square cross section. The convex polygonal cross section has a smaller bounded area so that in effect, the transition from a circular or elliptical cross section to a convex polygonal cross section creates a sealed friction-fit connection as the oral tip (not shown) is inserted into the connection port 754 to prevent leakage. In one embodiment, the convex polygonal cross section is sized and shaped so that the luer tip (not shown) does not seal with the convex polygonal cross section. In the illustrated embodiment, the adaptor 710 includes a stop 768 having channels 770 and a contact surface 772 to further prevent a butt seal of a luer tip with the bottom of the connection port 754, although it is contemplated that the stop and the channels are optional as the convex polygonal cross section may be sufficient to prevent a sealed connection and promote leakage.

Figure 25:
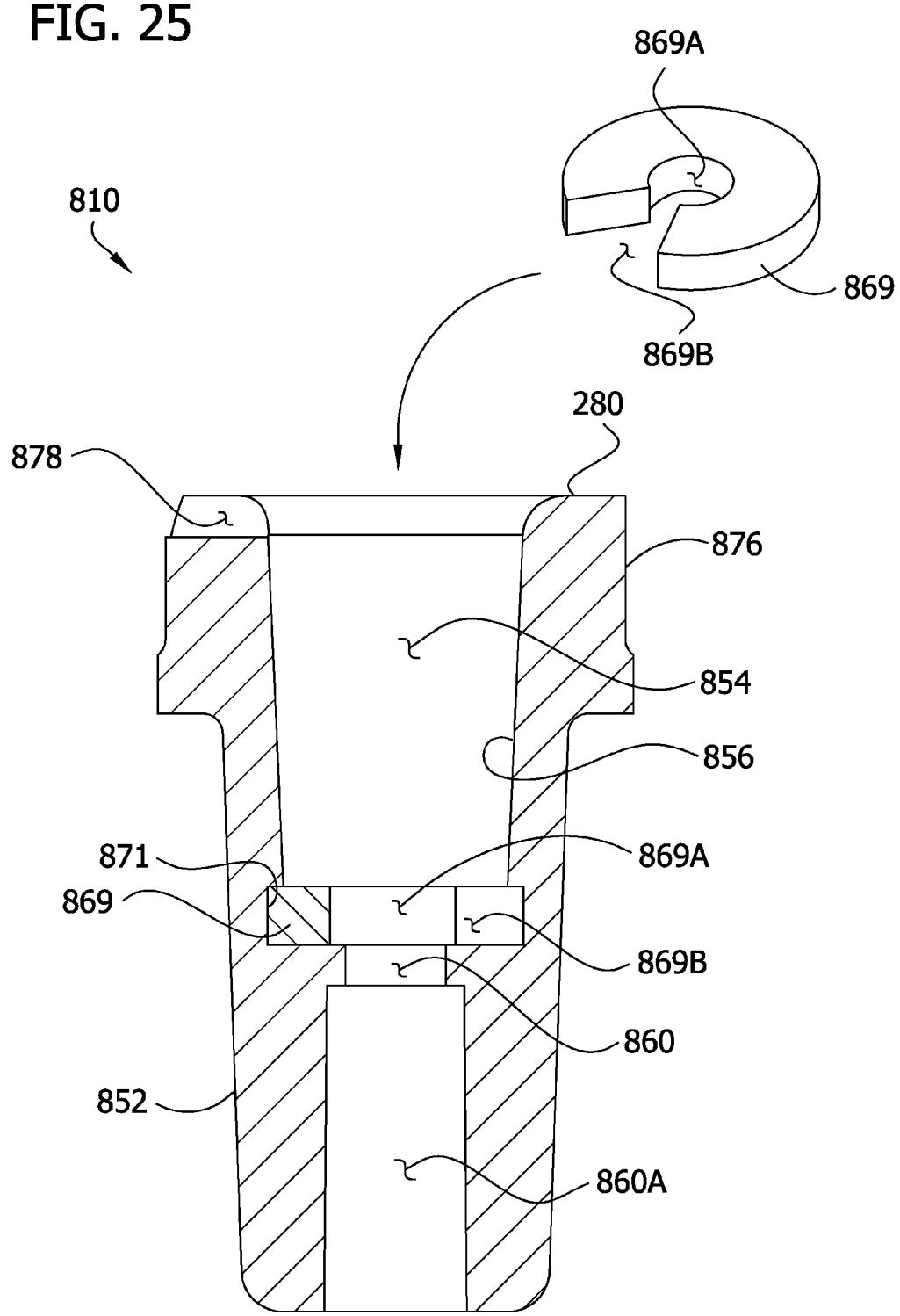
FIG. 25 is a section of a tenth embodiment of the discriminating oral-tip adaptor.

Referring to FIG. 25, a tenth embodiment of the adaptor is generally indicated at 810. This embodiment is similar to the second embodiment, and therefore, like components are indicated by corresponding reference numbers plus 800. The difference between the second embodiment and the present adaptor 810 is that the present adaptor includes an insert 869 secured within the connection port 854 and functioning as the internal stop. A second insert is shown exploded from the adaptor body 852 and in perspective in FIG. 25 to more fully illustrate the insert. The insert 869 is generally rigid relative to the adaptor body 852 to prevent the standard luer tip 44 from digging into or elastically deforming the adaptor body and forming a fluid-tight seal. The insert 869 is generally annular and is received in an annular groove 871 in the interior wall 856 of the adaptor body 852 adjacent to the end of the connection port 854 inside the body. The insert 869 may be secured within the connection port 854 by overmolding and/or by adhesive. The insert 869 has a generally open ring shape with an axial opening 869A and a radial cutout 869B. The diameter of the axial opening 869A is less than the cross-sectional diameter of the free end of the standard luer tip so that the luer tip cannot enter the opening. The axial cutout 869B prevents a butt seal between the standard luer tip and the rigid insert 869. Thus, liquid delivered via a standard luer tip 44 will leak out the first open end of the adaptor body 852 because the standard luer tip does not seal with the interior wall 856 defining the connection port 854. Liquid delivered via an oral tip does not leak out the first open end of the adaptor body 852 because the oral tip seals with the interior wall 856 defining the connection port 854. The insert 810 may be of other shapes and sizes, and may be secured within the connection port 854 in other ways.

Figure 26A:
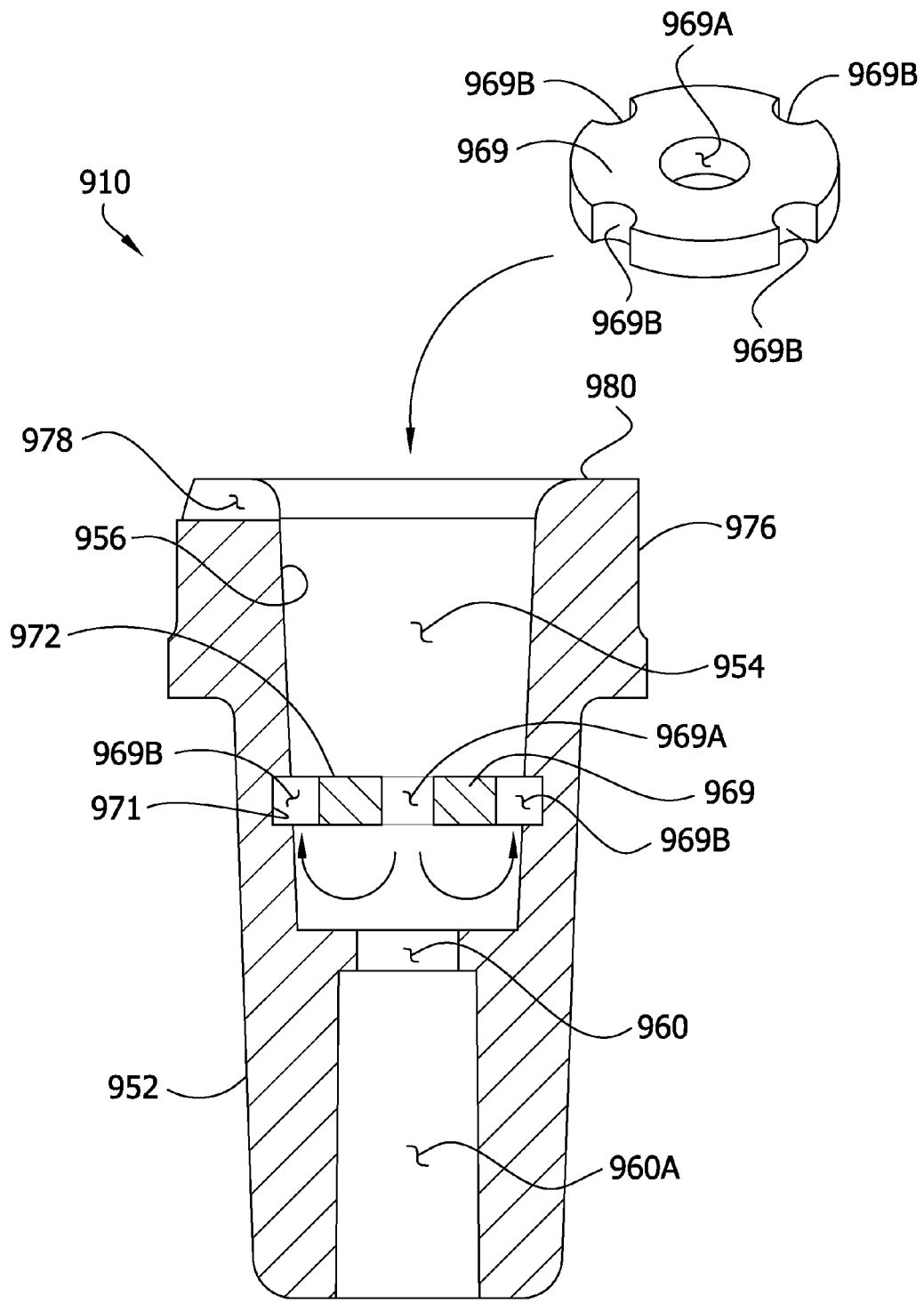
FIG. 26A is a section of a first example of an eleventh embodiment of the discriminating oral-tip adaptor.

Referring to FIGS. 26A and 26B, an eleventh embodiment of the adaptor is generally indicated at 910. This embodiment is similar to the tenth embodiment, and therefore, like components are indicated by corresponding reference numbers plus 100. The difference between the tenth embodiment and the present adaptor 910 is that the insert 969 in the present adaptor is of a different shape and is spaced longitudinally from the outlet passage 960. The insert 969 in the present embodiment has an axial opening 969A having a diameter less than the cross-sectional diameter of the luer tip 44, and a plurality of spaced apart radial cutouts 969B spaced radially from the axial opening. As shown by arrows in FIG. 26A, by spacing the insert from the outlet passage 960, at least some of the liquid delivered by the luer-lock component 44 flows through the axial opening 969A into the space between the insert and the outlet passage, flows radially within the space, flows through the radial cutouts 969B, and flows between the luer tip and the interior wall 956 defining the connection port 954, and exits the adaptor 910 at the first open end of the adaptor body 952. Liquid delivered via an oral tip 40 does not leak out the first open end of the adaptor body 952 because the oral tip seals with the interior wall 956 defining the connection port 954.

Figure 27:
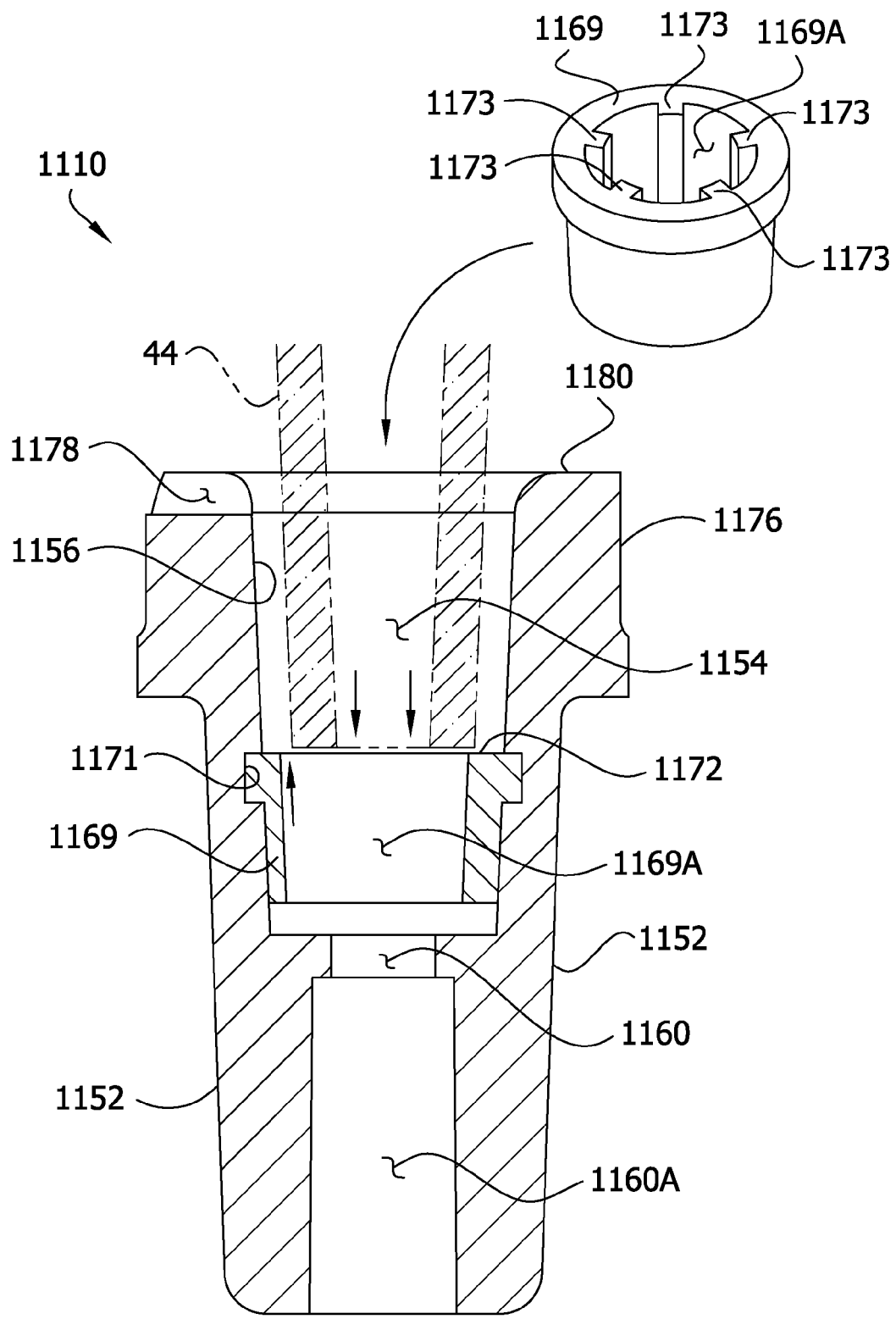
FIG. 27 is a section of a third example of the eleventh embodiment of the discriminating oral-tip adaptor.

It is understood that the insert 910 may have other configurations, including the configuration in FIG. 25, and the configurations shown in FIGS. 26B and 27. An insert 1010 in FIG. 26B has an X-shape and does not include an axial opening. Liquid flows between arms of the X-shaped insert 1069. An insert 1169 in FIG. 27 is generally cylindrical and includes spaced apart ribs 1173 extending radially inward from an interior surface of the insert. The ribs 1173 define longitudinal channels 11 69A that prevent a luer tip from making a sealed connection with the insert 1169. It is also understood that insert may have a leg(s) projecting longitudinally toward the outlet passage and contacting the end of the connection port. Other configurations of the insert are within the scope of the invention.

Figure 28:
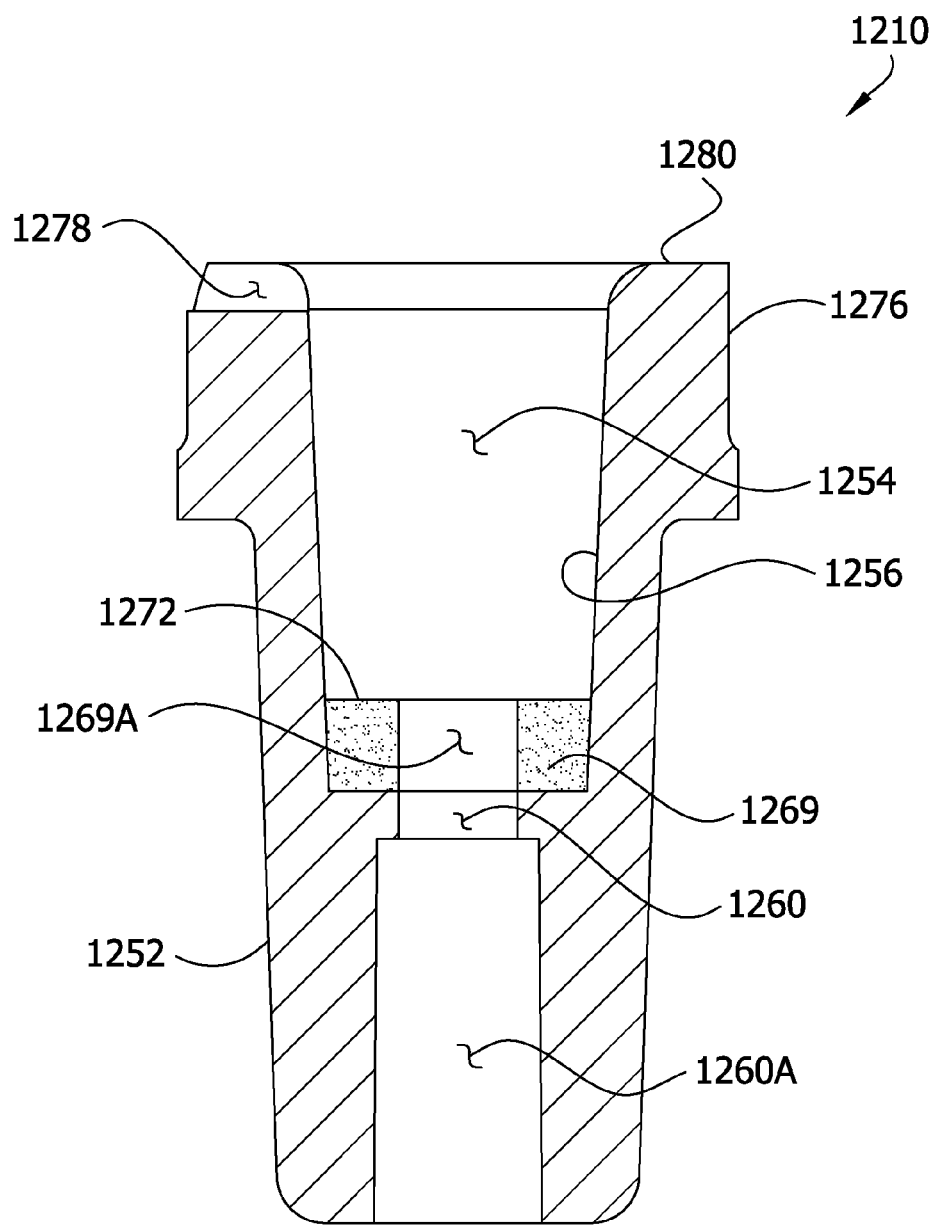
FIG. 28 is a section of an twelfth embodiment of the discriminating oral-tip adaptor.

Referring to FIG. 28, a twelfth embodiment of the adaptor is generally indicated at 1210. This embodiment is similar to the tenth embodiment, and therefore, like components are indicated by corresponding reference numbers plus 400. The difference between the tenth embodiment and the adaptor 1210 is that the insert 1269 of the present adaptor is formed from a liquid-permeable material. The liquid-permeable insert 1269 is generally annular and has an axial opening 1269A. A diameter of the axial opening 1269A is less than the cross-sectional diameter of the free end of the standard luer tip so that the luer tip contacts the contact surface 1272 and does not enter the axial opening. When the luer tip is inserted into the connection port 1254 and liquid is delivered via a luer tip, the liquid flows radially through the liquid-permeable insert 1269 and leaks out the first open end of the adaptor body 1252. Liquid delivered via an oral tip does not leak out the first open end of the adaptor body 1252 because the oral tip seals with the interior wall 1256 defining the connection port 1254.

Figure 29:
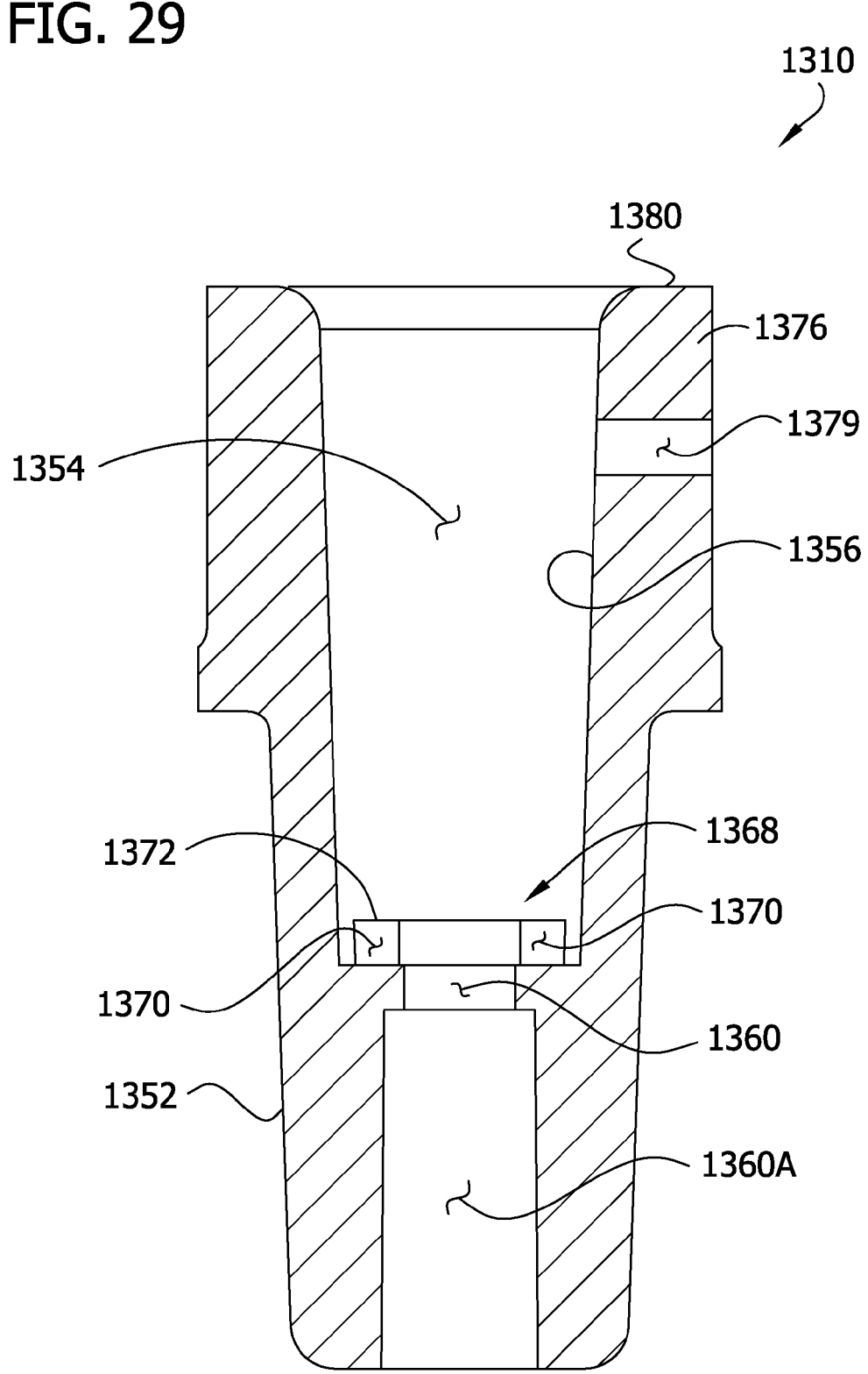
FIG. 29 is a section of a thirteenth embodiment of the discriminating oral-tip adaptor.

Referring to FIG. 29, a thirteenth embodiment of the adaptor is generally indicated at 1310. This embodiment is similar to the second embodiment, and therefore, like components are indicated by corresponding reference numbers plus 1300. The difference between the second embodiment and the present adaptor 1310 is that the present adaptor has a release opening 1379 extending generally radially from the connection port 1354 through the adaptor body 1352, as opposed to having the release channel formed in the contact surface 1380 of the external stop 1376. In this embodiment, the release opening 1379 is spaced longitudinally from the first open end of the adaptor body 1352. An oral tip extends past the release opening 1379 when component is inserted into the connection port 1354 and sealed with the interior wall 1356. Accordingly, in use the oral tip is not in fluid communication with the release opening 1379. If a luer tip 44 is used to deliver liquid, at least some of the liquid will flow out the release opening 1379 in the same manner as it would flow through channels 1370 and out the release channel in the previous embodiments. Moreover, if a luer-lock sleeve is used with the luer tip, the luer-lock sleeve does not prevent liquid from leaking out the release opening 1379. It is contemplated that the adaptor 1310 may include more than one release opening 1379.

Figure 30:
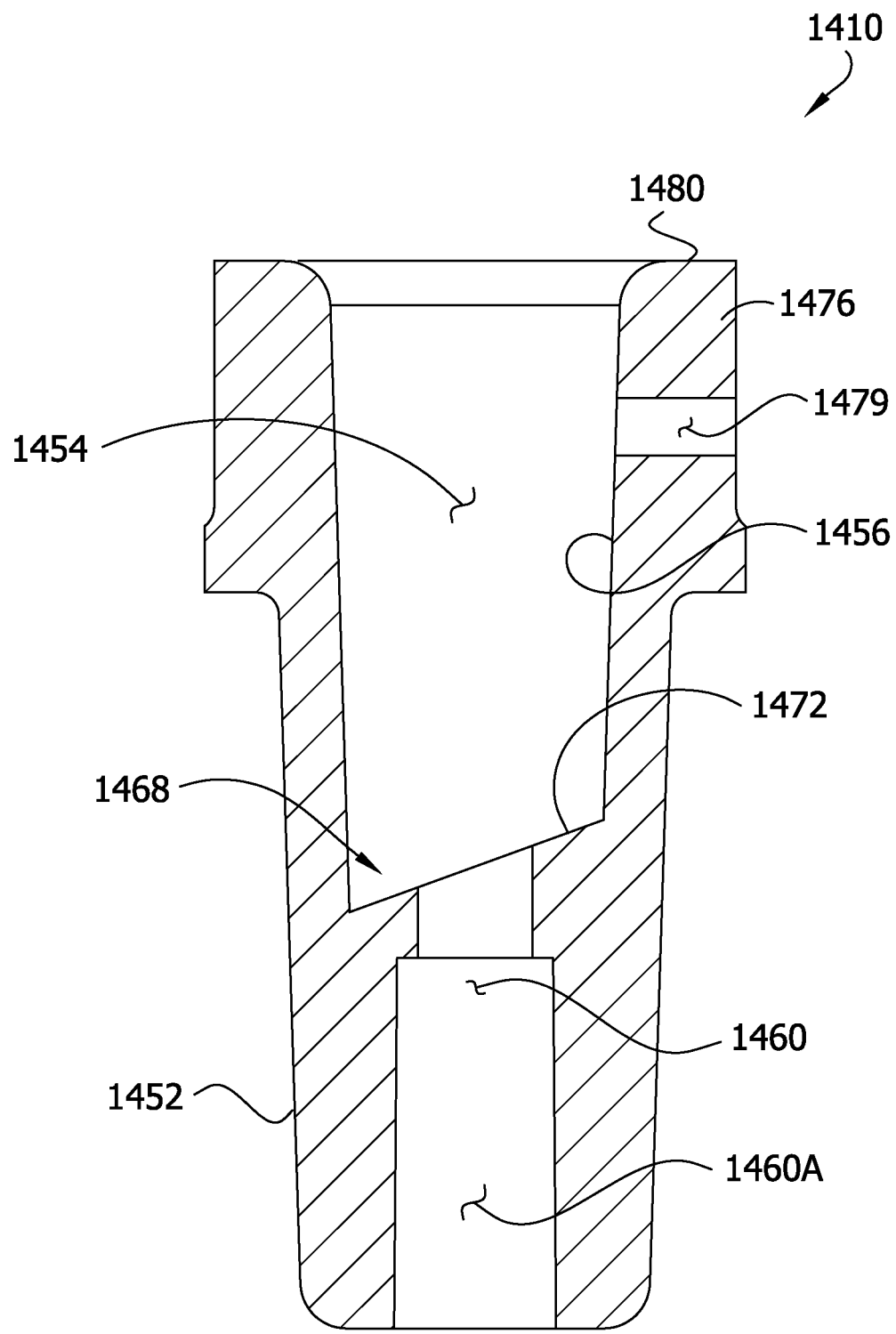
FIG. 30 is a section of a fourteenth embodiment of the discriminating oral-tip adaptor.

It is contemplated that the release opening 1379 of the present adaptor 1310 may be incorporated in any of the other embodiments described herein in lieu of the release channel or may be incorporated in other adaptors not explicitly disclosed herein. For example, referring to FIG. 30, a fourteenth embodiment of the adaptor is generally indicated at 1410. This adaptor 1410 is essentially a combination of the sixth and fourteenth embodiments. The adaptor 1410 has an angled contact surface, like the sixth embodiment, and a release opening 1479 in lieu of the release channel, like the fourteenth embodiment.

Figure 31:
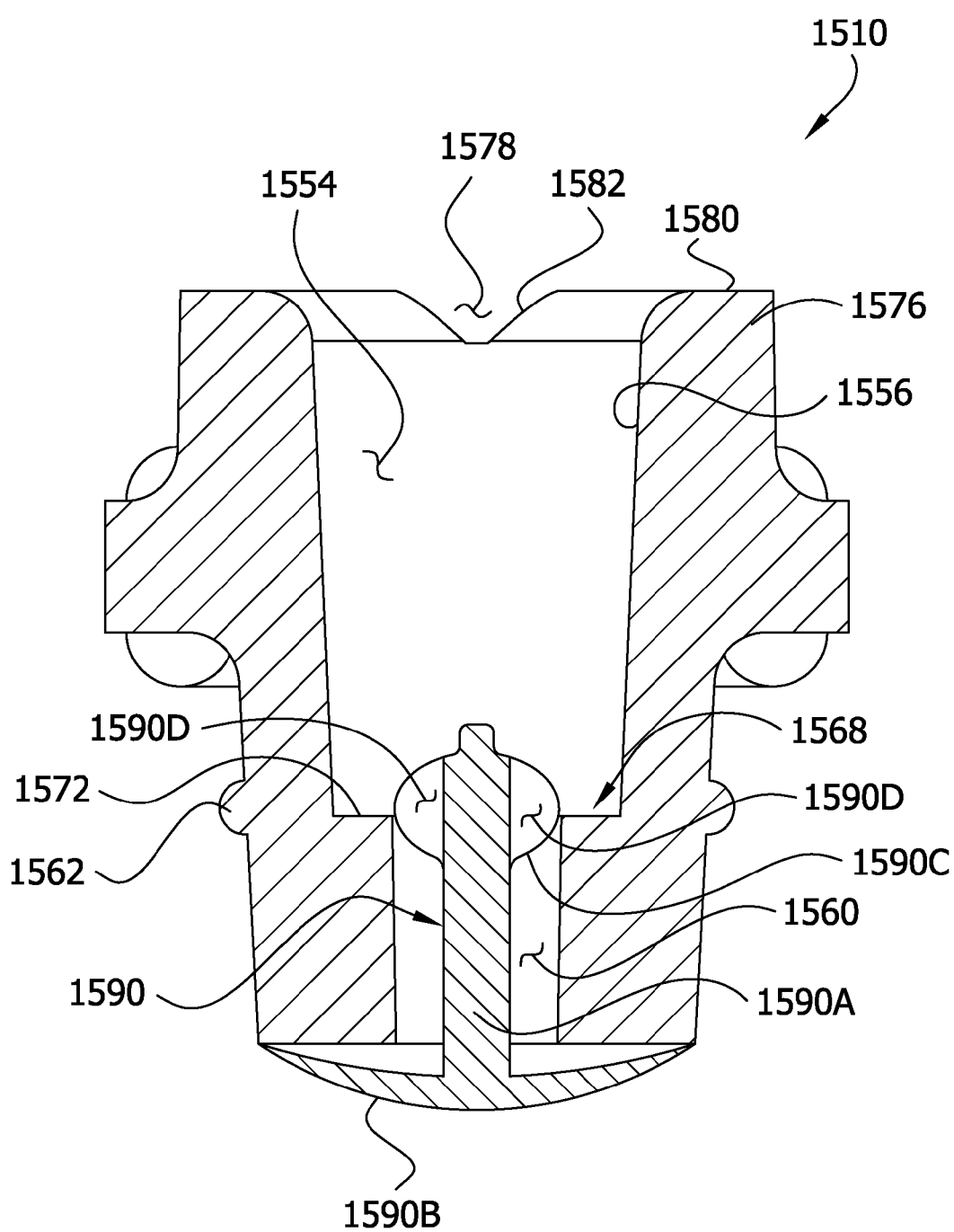
FIG. 31 is a section of an fifteenth embodiment of the discriminating oral-tip adaptor.

Referring to FIG. 31, a fifteenth embodiment of the adaptor is generally indicated at 1510. This embodiment is similar to the first embodiment, and therefore, like components are indicated by corresponding reference numbers plus 1500. The difference between the first embodiment and the adaptor 1510 is that the present adaptor does not have channels in a contact surface inside the connection port, but instead the present adaptor includes a valve, generally designated 1590, at the outlet passage 1560 that prevents liquid delivered via the standard-luer tip component from flowing through the outlet passage. In the illustrated embodiment, the valve 1590 includes a stem 1590A extending through the outlet passage. An umbrella seal 1590B extending radially outward from a first end of the stem 1590A seals the second open end of the adaptor body 1552 outside the adaptor body. The umbrella seal 1590B comprises a disk-like component that is elastically deformable. A shoulder 1590C extending radially outward at a second end of the stem 1590A is received in the connection port 1554 to secure the valve 1590 within the outlet passage 1560. The shoulder 1590C has radial slots 1590D to allow liquid to pass into the outlet passage 1560.

In use, if a standard luer tip 1544 is improperly inserted into the connection port 1554 and liquid is delivered via the luer tip, the umbrella seal 1590B prevents the liquid from exiting the outlet passage, and the liquid flows toward the first open end of the adaptor body 1552 and out the release channel 1578. If the oral tip 1540 is inserted into the connection port 1554 and liquid is delivered via the oral tip, the liquid pressure will build because unlike the standard luer tip, the oral tip is sealed with the interior wall 1556 of the body 1552 and liquid cannot flow between the oral tip and the interior wall. The pressure on the umbrella seal 1590B causes a circumferential edge margin of the umbrella seal to flip outward (i.e., elastically deform) or unseat from the second open end of the adaptor body 1552. Accordingly, liquid will pass between the umbrella seal 1590B and the second open end of the adaptor body 1552.

Figure 32:
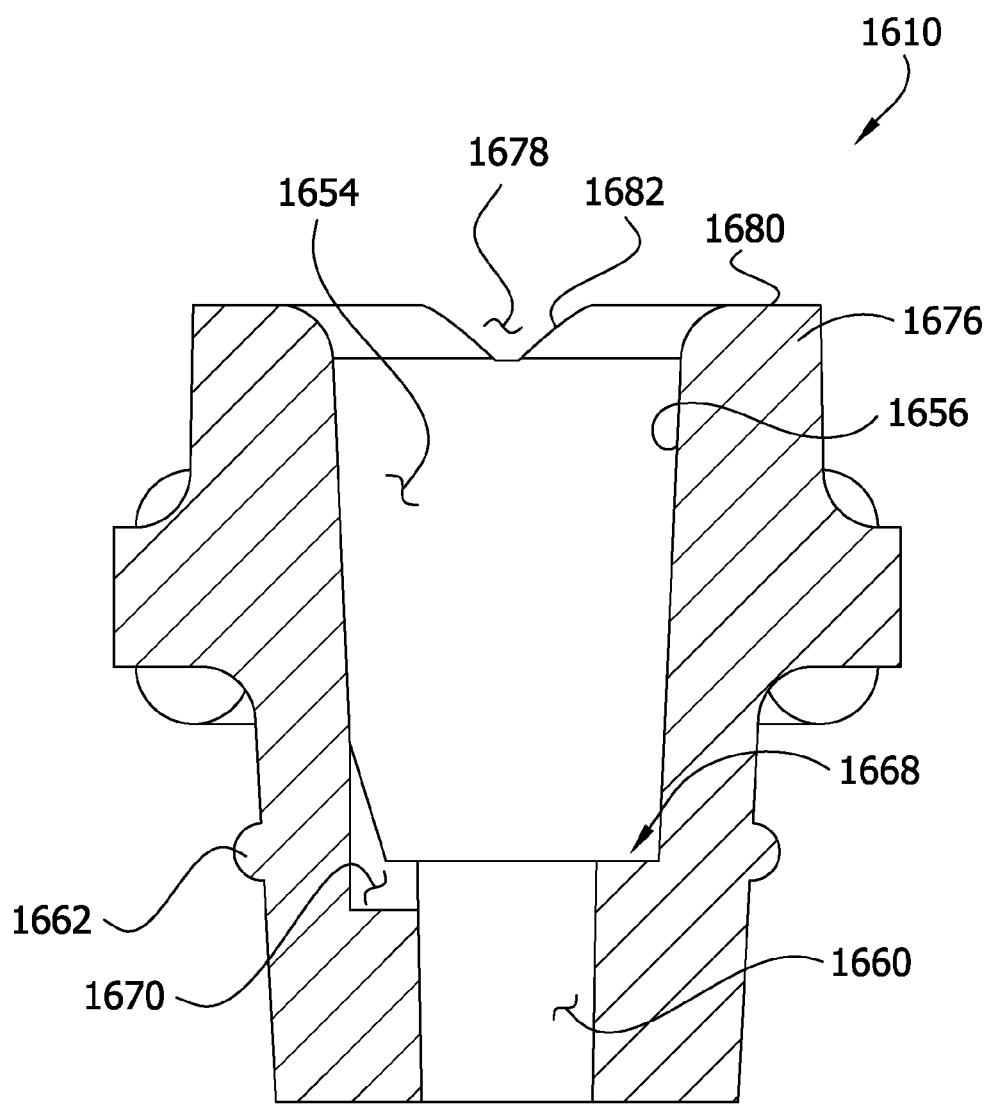
FIG. 32 is a section of a sixteenth embodiment of the discriminating oral-tip adaptor.

Referring to FIG. 32, a sixteenth embodiment of the adaptor is generally indicated at 1610. This embodiment is similar to the first embodiment, and therefore, like components are indicated by corresponding reference numbers plus 1600. The difference between the first embodiment and the present adaptor 1610 is that the channel 1670 in the present adaptor is generally shaped as a spline-cut through the internal stop 1668. The spline-cut channel 1670 functions in substantially the same manner as the channels in the first embodiment.

Figure 33:
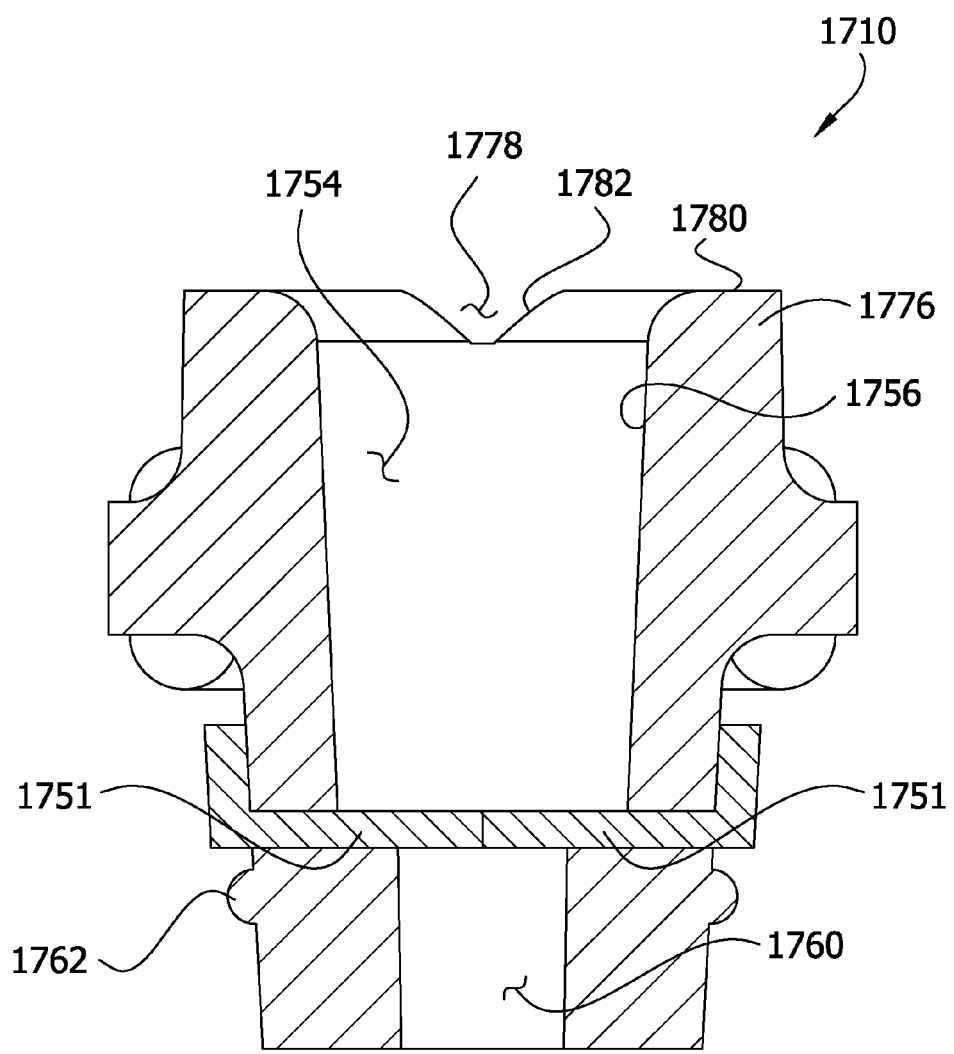
FIG. 33 is a section of a seventeenth embodiment of the discriminating oral-tip adaptor.

Referring to FIG. 33, a seventeenth embodiment of the adaptor is generally indicated at 1710. This embodiment is similar to the first embodiment, and therefore, like components are indicated by corresponding reference numbers plus 1700. The difference between the first embodiment and the present adaptor 1710 is that the second adaptor includes baffle plates 1751 at the end of the connection port 1754 within the adaptor body 1752. The baffle plates 1751 extend radially inward from outside the adaptor body 1752 and overlap or abut within the connection port 1754 to seal the connection port from the outlet passage 1760. When an oral tip is inserted into the connection port 1754, the component engages the interior wall 1756 so that the adaptor body 1752 elastically expands radially. The baffle plates 1751 move radially apart from one another as the adaptor body 1752 expands radially so that the connection port 1754 and the outlet passage 1760 are in fluid communication and liquid delivered via the oral tip flows through the outlet passage. In contrast, when a standard luer tip is inserted into the connection port 1754, the adaptor body 1752 does not expand radially because the diameter of the luer tip does not engage the interior wall 1756 of the body. As such, the baffle plates 1751 remain in their overlapping or abutting configuration and the connection port 1754 remains sealed from the outlet passage 1760. Liquid delivered via the luer tip will flow toward the first open end of the adaptor body 1752 and through the release channel 1778.

Figure 34:
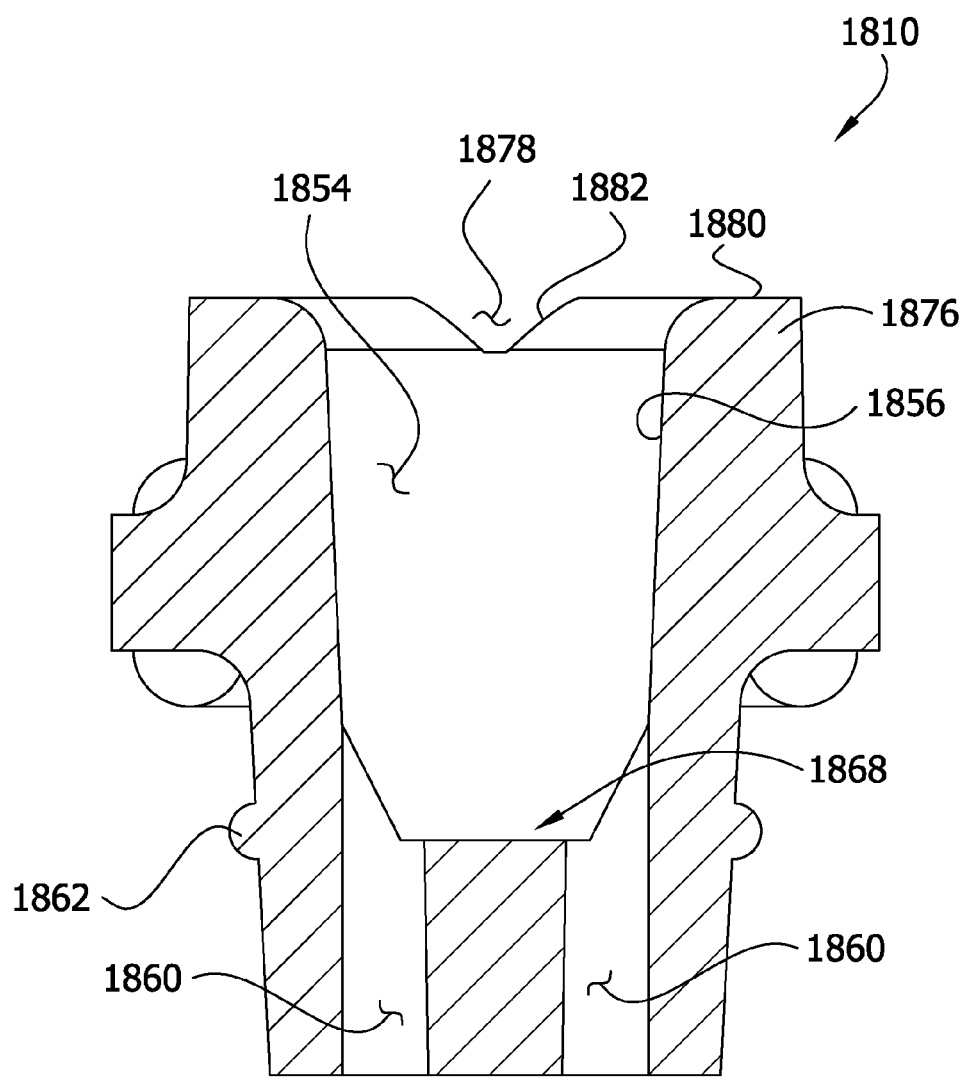
FIG. 34 is a section of an eighteenth embodiment of the discriminating oral-tip adaptor.

Referring to FIG. 34, an eighteenth embodiment of the adaptor is generally indicated at 1810. This embodiment is similar to the seventh embodiment, and therefore, like components are indicated by corresponding reference numbers plus 1300. The difference between the seventh embodiment and the present adaptor 1810 is that the present adaptor has two or more outlet passages 1860 that are offset from the longitudinal axis of the connection port 1854.

Figure 35:
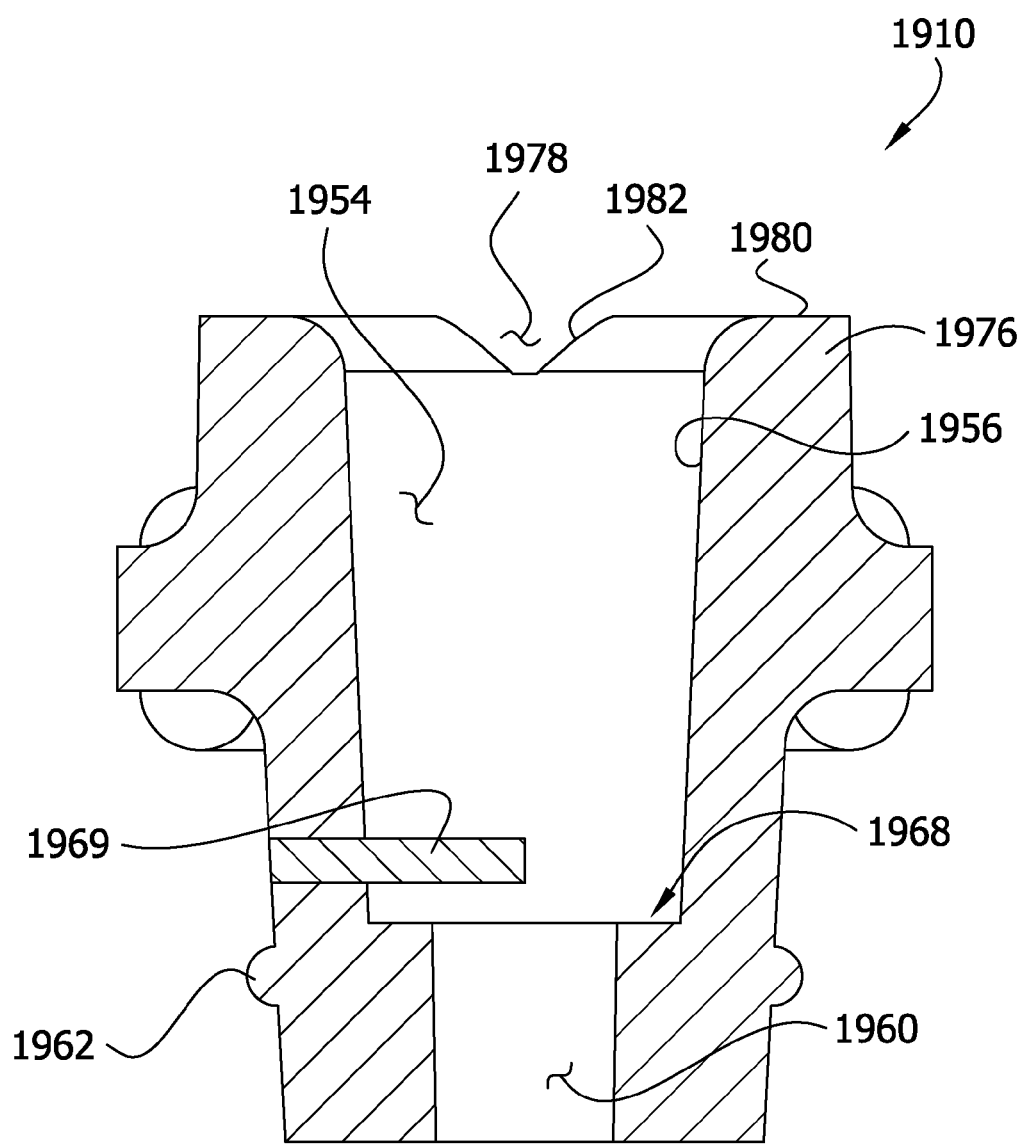
FIG. 35 is a section of a nineteenth embodiment of the discriminating oral-tip adaptor.

Referring to FIG. 35, a nineteenth embodiment of the adaptor is generally indicated at 1910. This embodiment is similar to the tenth embodiment, and therefore, like components are indicated by corresponding reference numbers plus 1100. The difference between the tenth embodiment and the present adaptor 1910 is that present adaptor includes an insert 1969 extending radially through the adaptor body 1952 into the connection port 1954. In the illustrated embodiment, the insert 1969 comprises a generally rigid shaft. Thus, liquid delivered via a standard luer tip 44 will leak out the first open end of the adaptor body 1952 because the standard luer tip cannot seal with the interior wall 1956 defining the connection port 1954 or butt seal with the stop 1968. Liquid delivered via the oral tip 40 does not leak out the first open end of the adaptor body 1952 because the oral tip seals with the interior wall 1956 above the insert 1969.

Figure 36:
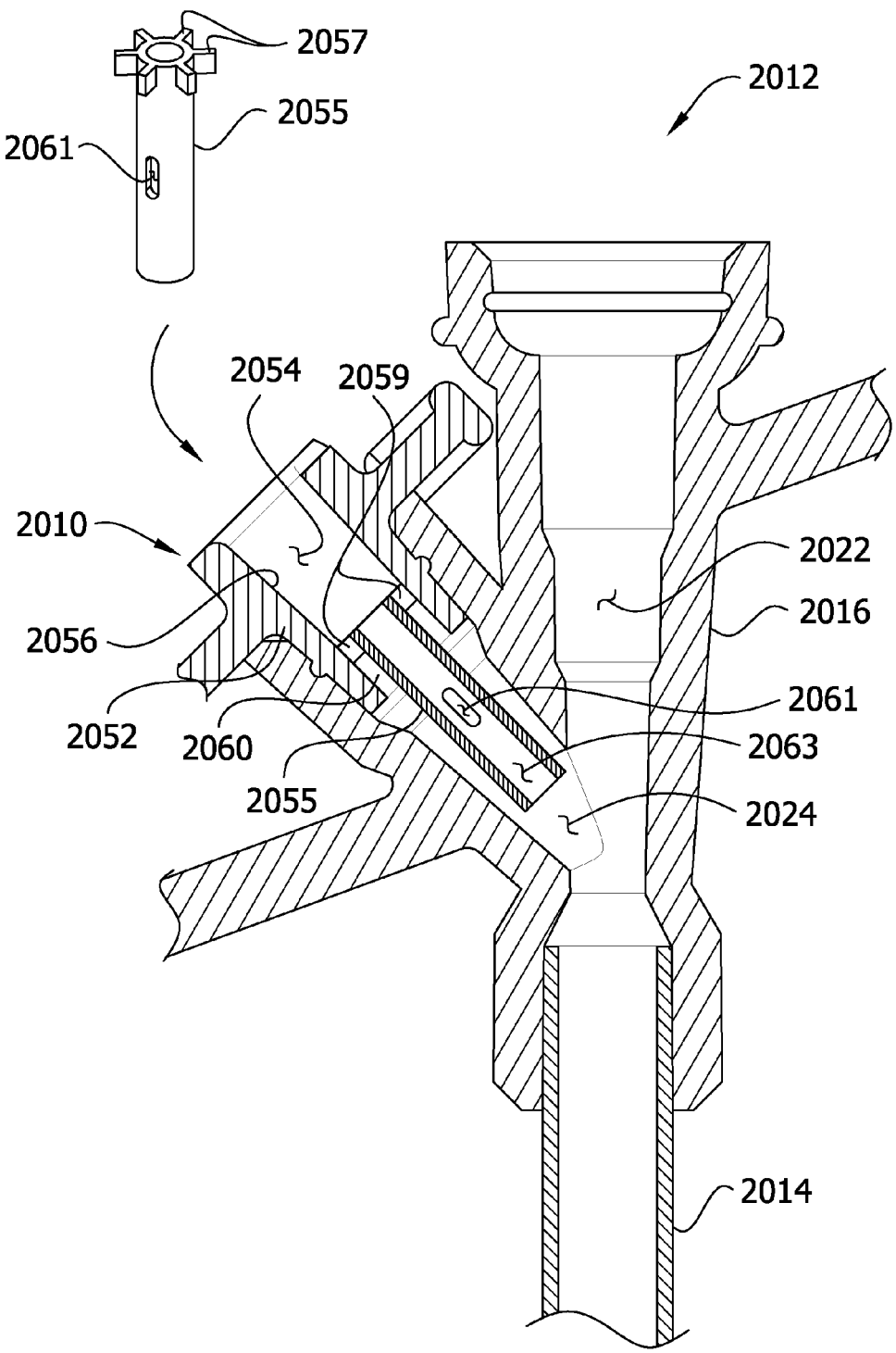
FIG. 36 is a section of a twentieth embodiment of the discrimination oral-tip adaptor.

Referring to FIG. 36, a twentieth embodiment of the adaptor is generally indicated at 2010. This embodiment is similar to the first embodiment, and therefore, like components are indicated by corresponding reference numbers plus 2000. The difference between the second embodiment and the adaptor 2010 is that the present adaptor includes a tube 2055 secured in the adaptor body 2052. The tube 2055 acts as a standoff that prevents a luer tip 44 (not shown) from sealing with the adaptor when the luer tip is inserted into the adaptor 2010. The tube 2055 includes spaced apart radial attachment members 2057 that are secured to the interior wall 2056 of the adaptor body 2052. The spaced apart radial attachment members define radial openings 2059 that allow fluid communication between the port 2054 and the outlet passage 2060. The tube includes at least one opening 2061 extending through the tube to an internal passage 2063.

When introducing elements of the present invention or the preferred embodiments thereof, the articles "a", "an", "the" and "said" are intended to mean that there are one or more of the elements. The terms "comprising", "including" and "having" are intended to be inclusive and mean that there may be additional elements other than the listed elements. Moreover, orientational terms like "upper" and "lower" are used for convenience and do not mandate any particular orientation of the thing described. Moreover, dimensions provided herein are exemplary only and not intended to limit the scope of the invention.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. In combination, a feeding line connector assembly and an adaptor for discriminating connection of an oral tip of a source of liquid enteral product to a feeding line and preventing sealed connection with a standard luer tip including a luer-lock sleeve, the feeding line connector assembly comprising:
    a primary section defining a main fluid passage; and
    a Y-port extending laterally outward from the primary section and defining an auxiliary fluid passage in fluid communication with the main fluid passage; and
    the adaptor comprising:
        a body having first and second open longitudinal ends;
        a connection port extending into the body from the first open end, the connection port being sized and shaped to sealingly receive an oral tip and to prevent sealing connection with the standard luer tip;
        a fluid outlet passage extending from the connection port inside the body to the second open end of the body; and
        an external stop surrounding the connection port generally adjacent to the first open end of the body, the external stop having a contact surface that is sized and shaped to prevent reception of the stop into a luer-lock sleeve of the standard luer tip so that the luer-lock sleeve generally abuts the external stop if the standard male luer tip is inserted into the connection port through the first open end, the external stop having a fluid release channel in fluid communication with the connection port extending generally radially through the external stop, the contact surface having a larger surface area than the projected area of the release channel in the plane of the contact surface;
    wherein the second open end of the adaptor is sized and shaped for sealed reception in the Y-port of the feeding line assembly; and
    wherein, in use, an outer surface of the body sealingly engages an inner surface of the Y-port.

2. The combination as set forth in claim 1 wherein the external stop has an external diameter greater than about 0.333 mm.

3. The combination as set forth in claim 2 wherein the external stop includes a single fluid release channel.

4. The combination as set forth in claim 3 wherein the width of the fluid release channel flares radially outward.

5. The combination as set forth in claim 3 wherein the adaptor further comprises an internal stop in the body having a contact surface configured to contact the standard luer tip inserted into the connection port and stop further insertion of the standard luer tip, the internal stop having a generally radially extending channel in the contact surface to prevent a butt-seal connection between the contact surface and the standard luer tip, the contact surface having a larger surface area than the projected area of the channel in the plane of the contact surface.

6. The combination as set forth in claim 1 further comprising a feeding tube, wherein the feeding tube is to the body of the adaptor adjacent to the second open end so that the feeding tube is in fluid communication with the fluid outlet passage in the adaptor.

7. The combination as set forth in claim 1, wherein the connection port is elastically deformable.

8. The combination as set forth in claim 1, wherein the feeding line connector assembly and the adaptor are formed as a one-piece, integral structure.

9. The combination as set forth in claim 1, wherein the adaptor is tethered to the feeding line connector.

10. An adaptor for discriminating connection of an oral tip of a source of liquid enteral product to a feeding line and preventing sealed connection with a standard luer tip including a luer-lock sleeve, the adaptor comprising:
    a body having first and second open longitudinal ends;
    a connection port extending into the body from the first open end, the connection port being sized and shaped to sealingly receive an oral tip and to prevent sealing connection with the standard luer tip;
    a fluid outlet passage extending from the connection port inside the body to the second open end of the body;
    an external stop surrounding the connection port generally adjacent to the first open end of the body, the external stop having a contact surface that is sized and shaped to prevent reception of the stop into a luer-lock sleeve of the standard luer tip so that the luer-lock sleeve generally abuts the external stop if the standard male luer tip is inserted into the connection port through the first open end, the external stop having a fluid release channel in fluid communication with the connection port extending generally radially through the external stop, the contact surface having a larger surface area than the projected area of the release channel in the plane of the contact surface; and
    an internal stop in the body having a contact surface including a radial dimension configured to contact the standard luer tip inserted into the connection port and stop further insertion of the standard luer tip, the internal stop having a generally radially extending channel in the contact surface extending through the entire radial dimension of the contact surface to prevent a butt-seal connection between the contact surface and the standard luer tip, the contact surface having a larger surface area than the projected area of the channel in the plane of the contact surface.

11. An adaptor for discriminating connection of an oral tip of a source of liquid enteral product to a feeding line and preventing sealed connection with a standard luer tip including a luer-lock sleeve, the adaptor comprising:
    a body having first and second open longitudinal ends;
    a connection port extending into the body from the first open end, the connection port being sized and shaped to sealingly receive an oral tip and to prevent sealing connection with the standard luer tip;

a fluid outlet passage extending from the connection port inside the body to the second open end of the body;

an external stop surrounding the connection port generally adjacent to the first open end of the body, the external stop having a contact surface that is sized and shaped to prevent reception of the stop into a luer-lock sleeve of the standard luer tip so that the luer-lock sleeve generally abuts the external stop if the standard male luer tip is inserted into the connection port through the first open end, the external stop having a fluid release channel in fluid communication with the connection port extending generally radially through the external stop, the contact surface having a larger surface area than the projected area of the release channel in the plane of the contact surface; and an internal stop in the body having a contact surface including a radial dimension configured to contact the standard luer tip inserted into the connection port and stop further insertion of the standard luer tip, the internal stop having a generally radially extending channel in the contact surface extending through the entire radial dimension of the contact surface to prevent a butt-seal connection between the contact surface and the standard luer tip, the contact surface having a larger surface area than the projected area of the channel in the plane of the contact surface;

wherein an outer surface of the body disposed opposite the connection port and adjacent the fluid outlet passage is configured to sealingly engage an inner surface of an adaptor-receiving port.

* * * * *